US012649950B2

(12) United States Patent　　　(10) Patent No.: US 12,649,950 B2
Jost et al.　　　(45) Date of Patent: *Jun. 9, 2026

(54) COMPOSITIONS AND METHODS FOR DETECTION OF VIRAL PATHOGENS IN SAMPLES

(71) Applicant: Gen-Probe Incorporated, San Diego, CA (US)

(72) Inventors: Matthias Jost, San Diego, CA (US); Pamela Douglass, Kansas City, MO (US); Daniel P. Kolk, Ramona, CA (US); Mehrdad R. Majlessi, Escondido, CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/625,354

(22) Filed: Apr. 3, 2024

(65) Prior Publication Data

US 2024/0240269 A1　　Jul. 18, 2024

Related U.S. Application Data

(62) Division of application No. 16/488,909, filed as application No. PCT/US2018/023995 on Mar. 23, 2018, now Pat. No. 11,976,337.

(60) Provisional application No. 62/476,659, filed on Mar. 24, 2017.

(51) Int. Cl.
*C12Q 1/6883*　　(2018.01)
*C12Q 1/70*　　(2006.01)

(52) U.S. Cl.
CPC ........... *C12Q 1/6883* (2013.01); *C12Q 1/701* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 4,683,202 A | 7/1987 | Mullis | |
| 5,834,254 A * | 11/1998 | Shen .................... | C12N 9/1241 |
| | | | 530/412 |
| 6,015,664 A | 1/2000 | Henrickson et al. | |
| 8,354,230 B2 | 1/2013 | Chen et al. | |
| 9,624,555 B2 | 4/2017 | Hellyer et al. | |
| 2004/0053275 A1 | 3/2004 | Shafer | |
| 2008/0003565 A1 * | 1/2008 | Baptista .................. | C12Q 1/70 |
| | | | 435/5 |
| 2010/0055672 A1 | 3/2010 | Saghbini | |
| 2010/0273156 A1 | 10/2010 | Hellyer et al. | |
| 2013/0059748 A1 | 3/2013 | Hully et al. | |
| 2013/0267429 A1 | 10/2013 | Gardner et al. | |

| | | | |
|---|---|---|---|
| 2014/0309138 A1 | 10/2014 | Poetter et al. | |
| 2016/0273057 A1 | 9/2016 | Roth | |
| 2019/0002994 A1 | 1/2019 | Jeon et al. | |

FOREIGN PATENT DOCUMENTS

| | | | |
|---|---|---|---|
| CN | 102337352 A | 2/2012 | |
| CN | 105400907 A | 3/2016 | |
| JP | 2006-180878 A | 7/2006 | |
| JP | 2011-103861 A | 6/2011 | |
| JP | 2012532627 A | 12/2012 | |
| JP | 201522104 A | 2/2015 | |
| JP | 2016131498 A | 7/2016 | |
| WO | WO 2007/064758 A2 | 6/2007 | |
| WO | WO 2007/130519 A2 | 11/2007 | |
| WO | WO 2008/086094 A2 | 7/2008 | |
| WO | WO 2008/140513 A1 | 11/2008 | |
| WO | WO 2009/085733 A1 | 7/2009 | |
| WO | WO 2009/085733 A4 | 7/2009 | |
| WO | WO 2013/006720 A2 | 1/2013 | |
| WO | WO 2016/004539 A1 | 1/2016 | |
| WO | WO 2016/028312 A1 | 2/2016 | |

OTHER PUBLICATIONS

Ahern, H. The Scientist. 9(15): 20-25; see, e.g., p. 22 (Year: 1995).*
Sigma-Aldrich. qPCR Technical Guide. Available via url: <gene-quantification.com/SIAL-qPCR-Technical-Guide.pdf> (Year: 2008).*
De-Paris, et al., "Optimization of one-step duplex real-time RT-PCR for detection of influenza and respiratory syncytial virus in nasopharyngeal aspirates," J Virol Methods, 186(1-2):189-92, doi: 10.1016/j.jviromet.2012.07.008, Epub Jul. 13, 2012, (Dec. 2012).
Jost, et al., "The modular approach to respiratory syndromic testing with the fully-automated novel Panther Fusion System," Journal of Clinical Virology, 82S, S1-S142, Abstract No. 171, Presentation at ESCV 2016: Poster 22, (2016).
Mahony, et al., "Development of a respiratory virus panel test for detection of twenty human respiratory viruses by use of multiplex PCR and a fluid microbead-based assay," J Clin Microbiol, 45(9):2965-70, doi: 10.1128/JCM.02436-06, Epub Jun. 27, 2007, (Sep. 2007).
Mahony, "Detection of respiratory viruses by molecular methods," Clin Microbiol Rev., 21(4):716-47, doi: 10.1128/CMR.00037-07, (Oct. 2008).
Adachi, et al., "Comparison of the IMDx influenza A virus, influenza B virus, and respiratory syncytial virus A/B assay on the m2000 platform with real-time reverse transcriptase PCR assays," J Clin Microbiol, 52(12):4441-2,doi: 10.1128/JCM.02565-14, Epub Oct. 1, 2014, (Dec. 2014).

(Continued)

*Primary Examiner* — Carla J Myers
(74) *Attorney, Agent, or Firm* — Jeffrey E. Landes; Alston & Bird LLP

(57) ABSTRACT

This disclosure concerns amplification primers, hybridization assay probes, compositions containing such primers and probes, and associated reagents, kits, and methods, that can be used to analyze samples for the presence of Influenza A virus, Influenza B virus, Respiratory Syncytial Virus A, and/or Respiratory Syncytial Virus B target nucleic acids.

24 Claims, No Drawings
Specification includes a Sequence Listing.

(56)           References Cited

OTHER PUBLICATIONS

Van Wesenbeeck et al., "Comparison of the FilmArray RP, Verigene RV, and Prodesse ProFlu/Fast Multiplex Platforms for Detection of Influenza Viruses in Clinical Samples from the 2011-2012 Influenza Season in Belgium," Journal of Clinical Microbiology, vol. 51, No. 9, p. 2977-2985, (Sep. 2013).

Raymond, et al., "Comparison of automated microarray detection with real-time PCR assays for detection of respiratory viruses in specimens obtained from children," J Clin Microbiol, 47(3):743-50, doi: 10.1128/JCM.01297-08, Epub Jan. 21, 2009, (Mar. 2009).

Li, et al., "The development of a GeXP-based multiplex reverse transcription-PCR assay for simultaneous detection of sixteen human respiratory virus types/subtypes," BMC Infect Dis, 12:189, doi: 10.1186/1471-2334-12-189, (Aug. 14, 2012).

Hologic, Inc., Panther Fusion® System Assay Performance, Flu A/B/RSV, AW-16832 Rev. 001, (Sep. 2017).

NCBI Database. Gen Bank Accession No. KC355801.1, Jan. 13, 2013, National Library of Medicine, NIH, available via URL: <ncbi.nlm.nih.gov/nuccore/KC355801.1/> (Year: 2013).

Dieffenbach et al., "General concepts for PCR primer design," PCR methods and Applications, vol. 3, pp. S30-S37, (1993).

Roux, "Optimization and troubleshooting in PCR," PCR Methods and Applications, vol. 4, pp. s185-s194, (1995).

Leal et al., "Comparative analysis of conventional PCR and real-time PCR to diagnose shrimp WSD," Brazilian Journal of Microbiology, 44, 3, 901-904, (2013).

European Examination Report mailed Sep. 2, 2021 in corresponding application No. 18718029.4 (9 pages).

Japanese Office Action mailed Sep. 8, 2020 in corresponding application No. 2019-552249 (12 pages).

Canadian Office Action mailed Jun. 11, 2020 in corresponding application No. 3,055,427 (4 pages).

International Preliminary Report on Patentability dated Sep. 24, 2019 in corresponding PCT application PCT/US2018/023995 (10 pages).

Japanese Office Action mailed May 17, 2021 in corresponding application No. 2019-552249 (15 pages).

U.S. Appl. No. 16/488,909 Restriction Requirement mailed Dec. 18, 2021.

U.S. Appl. No. 16/488,909 Non-Final Office Action mailed May 16, 2022.

U.S. Appl. No. 16/488,909 Final Office Action mailed Jan. 19, 2023.

U.S. Appl. No. 16/488,909 Non-Final Office Action mailed Aug. 2, 2023.

U.S. Appl. No. 16/488,909 Notice of Allowance mailed Jan. 17, 2024.

Japanese Application No. 2024-070439, Office Action mailed Jun. 11, 2025.

NCBI Database GenBank Accession No. AY581980, Influenza B virus (B/Nebraska/1/01) M1 matrix protein (M1) and BM2 protein (BM2) genes, complete cds, National Library of Medicine, NIH, Bethesda, MD, 2 pgs., (2004).

Thermo Fisher Scientific (Milwaukee) LLC, Thermo Scientific Modified Nucleoside Phosphoramidites, 2 pgs., (2007).

U.S. Appl. No. 18/625,370, Final Office Action mailed Nov. 21, 2025.

U.S. Appl. No. 18/625,400, Final Office Action mailed Nov. 21, 2025.

U.S. Appl. No. 18/625,389, Non-Final Office Action mailed Nov. 25, 2025.

* cited by examiner

SEQUENCE LISTING

```
Sequence total quantity: 119
SEQ ID NO: 1              moltype = DNA  length = 18
FEATURE                   Location/Qualifiers
misc_feature              1..18
                          note = Synthetic Oligonucleotide
source                    1..18
                          mol_type = other DNA
                          organism = synthetic construct
SEQUENCE: 1
gatcttgagg ctctcatg                                              18

SEQ ID NO: 2              moltype = DNA  length = 20
FEATURE                   Location/Qualifiers
misc_feature              1..20
                          note = Synthetic Oligonucleotide
source                    1..20
                          mol_type = other DNA
                          organism = synthetic construct
SEQUENCE: 2
ataacrttcc atggrgccaa                                            20

SEQ ID NO: 3              moltype = DNA  length = 20
FEATURE                   Location/Qualifiers
misc_feature              1..20
                          note = Synthetic Oligonucleotide
source                    1..20
                          mol_type = other DNA
                          organism = synthetic construct
SEQUENCE: 3
ataacrttcc atggggccaa                                            20
```

-continued

```
SEQ ID NO: 4          moltype = DNA   length = 19
FEATURE               Location/Qualifiers
misc_feature          1..19
                      note = Synthetic Oligonucleotide
source                1..19
                      mol_type = other DNA
                      organism = synthetic construct
SEQUENCE: 4
ataacgttcc atggrgcca                                            19

SEQ ID NO: 5          moltype = DNA   length = 20
FEATURE               Location/Qualifiers
misc_feature          1..20
                      note = Synthetic Oligonucleotide
source                1..20
                      mol_type = other DNA
                      organism = synthetic construct
SEQUENCE: 5
ataacgttcc atgggggccaa                                          20

SEQ ID NO: 6          moltype = DNA   length = 20
FEATURE               Location/Qualifiers
misc_feature          1..20
                      note = Synthetic Oligonucleotide
source                1..20
                      mol_type = other DNA
                      organism = synthetic construct
SEQUENCE: 6
cccttagtca gaggtgacag                                           20

SEQ ID NO: 7          moltype = DNA   length = 27
FEATURE               Location/Qualifiers
misc_feature          1..27
                      note = Synthetic Oligonucleotide
source                1..27
                      mol_type = other DNA
                      organism = synthetic construct
SEQUENCE: 7
tcaggccccc tcaaagccga gatcgcc                                   27

SEQ ID NO: 8          moltype = DNA   length = 26
FEATURE               Location/Qualifiers
misc_feature          1..26
                      note = Synthetic Oligonucleotide
source                1..26
                      mol_type = other DNA
                      organism = synthetic construct
SEQUENCE: 8
tcaggccccc tcaaagccga ratcgc                                    26

SEQ ID NO: 9          moltype = DNA   length = 26
FEATURE               Location/Qualifiers
misc_feature          1..26
                      note = Synthetic Oligonucleotide
source                1..26
                      mol_type = other DNA
                      organism = synthetic construct
SEQUENCE: 9
tcaggccccc tcaaagccga gatcgc                                    26

SEQ ID NO: 10         moltype = DNA   length = 26
FEATURE               Location/Qualifiers
misc_feature          1..26
                      note = Synthetic Oligonucleotide
source                1..26
                      mol_type = other DNA
                      organism = synthetic construct
modified_base         5..6
                      mod_base = OTHER
                      note = uracil
modified_base         12..14
                      mod_base = OTHER
                      note = uracil
modified_base         24
                      mod_base = OTHER
                      note = uracil
SEQUENCE: 10
gcgatttcgg ctttgagggg gcctga                                    26
```

-continued

```
SEQ ID NO: 11              moltype = DNA   length = 26
FEATURE                    Location/Qualifiers
misc_feature               1..26
                           note = Synthetic Oligonucleotide
source                     1..26
                           mol_type = other DNA
                           organism = synthetic construct
modified_base              5
                           mod_base = OTHER
                           note = uracil
modified_base              12..14
                           mod_base = OTHER
                           note = uracil
modified_base              24
                           mod_base = OTHER
                           note = uracil
SEQUENCE: 11
gcgatctcgg ctttgagggg gcctga                                       26

SEQ ID NO: 12              moltype = DNA   length = 27
FEATURE                    Location/Qualifiers
misc_feature               1..27
                           note = Synthetic Oligonucleotide
source                     1..27
                           mol_type = other DNA
                           organism = synthetic construct
modified_base              6
                           mod_base = OTHER
                           note = uracil
SEQUENCE: 12
agccattcca tgagagcctc aagatcc                                      27

SEQ ID NO: 13              moltype = DNA   length = 26
FEATURE                    Location/Qualifiers
misc_feature               1..26
                           note = Synthetic Oligonucleotide
source                     1..26
                           mol_type = other DNA
                           organism = synthetic construct
SEQUENCE: 13
agccaytcca tragagcctc aagatc                                       26

SEQ ID NO: 14              moltype = DNA   length = 26
FEATURE                    Location/Qualifiers
misc_feature               1..26
                           note = Synthetic Oligonucleotide
source                     1..26
                           mol_type = other DNA
                           organism = synthetic construct
modified_base              6
                           mod_base = OTHER
                           note = uracil
SEQUENCE: 14
agccattcca tgagagcctc aagatc                                       26

SEQ ID NO: 15              moltype = RNA   length = 26
FEATURE                    Location/Qualifiers
source                     1..26
                           mol_type = other RNA
                           organism = synthetic construct
SEQUENCE: 15
gatcttgagg ctctcatgga gtggct                                       26

SEQ ID NO: 16              moltype = RNA   length = 26
FEATURE                    Location/Qualifiers
source                     1..26
                           mol_type = other RNA
                           organism = synthetic construct
SEQUENCE: 16
gatcttgagg ctctcatgga atggct                                       26

SEQ ID NO: 17              moltype = RNA   length = 26
FEATURE                    Location/Qualifiers
source                     1..26
                           mol_type = other RNA
                           organism = synthetic construct
SEQUENCE: 17
gatcttgagg ctcttatgga atggct                                       26
```

-continued

```
SEQ ID NO: 18           moltype = DNA   length = 24
FEATURE                 Location/Qualifiers
misc_feature            1..24
                        note = Synthetic Oligonucleotide
source                  1..24
                        mol_type = other DNA
                        organism = synthetic construct
modified_base           20
                        mod_base = OTHER
                        note = uracil
SEQUENCE: 18
ctggtgcact tgccagttgt atgc                                        24

SEQ ID NO: 19           moltype = DNA   length = 23
FEATURE                 Location/Qualifiers
misc_feature            1..23
                        note = Synthetic Oligonucleotide
source                  1..23
                        mol_type = other DNA
                        organism = synthetic construct
SEQUENCE: 19
ctggtgcact tgccagttcy atg                                         23

SEQ ID NO: 20           moltype = DNA   length = 23
FEATURE                 Location/Qualifiers
misc_feature            1..23
                        note = Synthetic Oligonucleotide
source                  1..23
                        mol_type = other DNA
                        organism = synthetic construct
modified_base           20
                        mod_base = OTHER
                        note = uracil
SEQUENCE: 20
ctggtgcact tgccagttct atg                                         23

SEQ ID NO: 21           moltype = RNA   length = 23
FEATURE                 Location/Qualifiers
source                  1..23
                        mol_type = other RNA
                        organism = synthetic construct
SEQUENCE: 21
catagaactg gcaagtgcac cag                                         23

SEQ ID NO: 22           moltype = RNA   length = 23
FEATURE                 Location/Qualifiers
source                  1..23
                        mol_type = other RNA
                        organism = synthetic construct
SEQUENCE: 22
catggaactg gcaagtgcac cag                                         23

SEQ ID NO: 23           moltype = DNA   length = 22
FEATURE                 Location/Qualifiers
misc_feature            1..22
                        note = Synthetic Oligonucleotide
source                  1..22
                        mol_type = other DNA
                        organism = synthetic construct
SEQUENCE: 23
cttctaaccg aggtcgaaac gt                                          22

SEQ ID NO: 24           moltype = DNA   length = 20
FEATURE                 Location/Qualifiers
misc_feature            1..20
                        note = Synthetic Oligonucleotide
source                  1..20
                        mol_type = other DNA
                        organism = synthetic construct
SEQUENCE: 24
ataacgttcc atggggccaa                                             20

SEQ ID NO: 25           moltype = DNA   length = 19
FEATURE                 Location/Qualifiers
misc_feature            1..19
                        note = Synthetic Oligonucleotide
source                  1..19
                        mol_type = other DNA
                        organism = synthetic construct
```

-continued

```
SEQUENCE: 25
cccttagtca gaggtgaca                                                    19

SEQ ID NO: 26          moltype = DNA   length = 20
FEATURE                Location/Qualifiers
misc_feature           1..20
                       note = Synthetic Oligonucleotide
source                 1..20
                       mol_type = other DNA
                       organism = synthetic construct
SEQUENCE: 26
cccattctgt tgtatatgag                                                   20

SEQ ID NO: 27          moltype = DNA   length = 20
FEATURE                Location/Qualifiers
misc_feature           1..20
                       note = Synthetic Oligonucleotide
source                 1..20
                       mol_type = other DNA
                       organism = synthetic construct
SEQUENCE: 27
cccatcctgt tgtatatgag                                                   20

SEQ ID NO: 28          moltype = DNA   length = 18
FEATURE                Location/Qualifiers
misc_feature           1..18
                       note = Synthetic Oligonucleotide
source                 1..18
                       mol_type = other DNA
                       organism = synthetic construct
SEQUENCE: 28
ggtgagcgtg aacacaaa                                                     18

SEQ ID NO: 29          moltype = DNA   length = 22
FEATURE                Location/Qualifiers
misc_feature           1..22
                       note = Synthetic Oligonucleotide
source                 1..22
                       mol_type = other DNA
                       organism = synthetic construct
SEQUENCE: 29
agtggaggat gaagaagatg gc                                                22

SEQ ID NO: 30          moltype = DNA   length = 33
FEATURE                Location/Qualifiers
misc_feature           1..33
                       note = Synthetic Oligonucleotide
source                 1..33
                       mol_type = other DNA
                       organism = synthetic construct
SEQUENCE: 30
gcctgctttg ccttctccat cttctgtgca ggc                                    33

SEQ ID NO: 31          moltype = DNA   length = 26
FEATURE                Location/Qualifiers
misc_feature           1..26
                       note = Synthetic Oligonucleotide
source                 1..26
                       mol_type = other DNA
                       organism = synthetic construct
SEQUENCE: 31
gcctgctttg ccttctccat cttctg                                            26

SEQ ID NO: 32          moltype = DNA   length = 34
FEATURE                Location/Qualifiers
misc_feature           1..34
                       note = Synthetic Oligonucleotide
source                 1..34
                       mol_type = other DNA
                       organism = synthetic construct
SEQUENCE: 32
gcctgctttg ccttctccat cttctgtagc aggc                                   34

SEQ ID NO: 33          moltype = DNA   length = 27
FEATURE                Location/Qualifiers
misc_feature           1..27
                       note = Synthetic Oligonucleotide
source                 1..27
                       mol_type = other DNA
```

-continued

```
                         organism = synthetic construct
SEQUENCE: 33
gcctgctttg ccttctccat cttctgt                                             27

SEQ ID NO: 34            moltype = DNA   length = 38
FEATURE                  Location/Qualifiers
misc_feature             1..38
                         note = Synthetic Oligonucleotide
source                   1..38
                         mol_type = other DNA
                         organism = synthetic construct
SEQUENCE: 34
gcgctagttc tgctttgcct tctccatctt cctagcgc                                 38

SEQ ID NO: 35            moltype = DNA   length = 31
FEATURE                  Location/Qualifiers
misc_feature             1..31
                         note = Synthetic Oligonucleotide
source                   1..31
                         mol_type = other DNA
                         organism = synthetic construct
SEQUENCE: 35
gcgctagttc tgctttgcct tctccatctt c                                        31

SEQ ID NO: 36            moltype = DNA   length = 38
FEATURE                  Location/Qualifiers
misc_feature             1..38
                         note = Synthetic Oligonucleotide
source                   1..38
                         mol_type = other DNA
                         organism = synthetic construct
SEQUENCE: 36
gcgctagttc tgctttgcct tctccatctt cctagcgc                                 38

SEQ ID NO: 37            moltype = DNA   length = 31
FEATURE                  Location/Qualifiers
misc_feature             1..31
                         note = Synthetic Oligonucleotide
source                   1..31
                         mol_type = other DNA
                         organism = synthetic construct
SEQUENCE: 37
gcgctagttc tgctttgcct tctccatctt c                                        31

SEQ ID NO: 38            moltype = DNA   length = 38
FEATURE                  Location/Qualifiers
misc_feature             1..38
                         note = Synthetic Oligonucleotide
source                   1..38
                         mol_type = other DNA
                         organism = synthetic construct
SEQUENCE: 38
gcgctagttc tgctttgcct tctccatctt cctagcgc                                 38

SEQ ID NO: 39            moltype = DNA   length = 31
FEATURE                  Location/Qualifiers
misc_feature             1..31
                         note = Synthetic Oligonucleotide
source                   1..31
                         mol_type = other DNA
                         organism = synthetic construct
SEQUENCE: 39
gcgctagttc tgctttgcct tctccatctt c                                        31

SEQ ID NO: 40            moltype = DNA   length = 34
FEATURE                  Location/Qualifiers
misc_feature             1..34
                         note = Synthetic Oligonucleotide
source                   1..34
                         mol_type = other DNA
                         organism = synthetic construct
SEQUENCE: 40
gctgctagtt ctgctttgcc ttctccatcg cagc                                     34

SEQ ID NO: 41            moltype = DNA   length = 29
FEATURE                  Location/Qualifiers
misc_feature             1..29
                         note = Synthetic Oligonucleotide
source                   1..29
```

-continued

```
                              mol_type = other DNA
                              organism = synthetic construct
SEQUENCE: 41
gctgctagtt ctgctttgcc ttctccatc                                  29

SEQ ID NO: 42          moltype = DNA   length = 36
FEATURE                Location/Qualifiers
misc_feature           1..36
                              note = Synthetic Oligonucleotide
source                 1..36
                              mol_type = other DNA
                              organism = synthetic construct
SEQUENCE: 42
gcctgctagt tctgctttgc cttctccatc gcaggc                          36

SEQ ID NO: 43          moltype = DNA   length = 30
FEATURE                Location/Qualifiers
misc_feature           1..30
                              note = Synthetic Oligonucleotide
source                 1..30
                              mol_type = other DNA
                              organism = synthetic construct
SEQUENCE: 43
gcctgctagt tctgctttgc cttctccatc                                 30

SEQ ID NO: 44          moltype = DNA   length = 36
FEATURE                Location/Qualifiers
misc_feature           1..36
                              note = Synthetic Oligonucleotide
source                 1..36
                              mol_type = other DNA
                              organism = synthetic construct
SEQUENCE: 44
gcctgctagt tctgctttgc cttctccatc gcaggc                          36

SEQ ID NO: 45          moltype = DNA   length = 30
FEATURE                Location/Qualifiers
misc_feature           1..30
                              note = Synthetic Oligonucleotide
source                 1..30
                              mol_type = other DNA
                              organism = synthetic construct
SEQUENCE: 45
gcctgctagt tctgctttgc cttctccatc                                 30

SEQ ID NO: 46          moltype = DNA   length = 37
FEATURE                Location/Qualifiers
misc_feature           1..37
                              note = Synthetic Oligonucleotide
source                 1..37
                              mol_type = other DNA
                              organism = synthetic construct
SEQUENCE: 46
gcctgctagt tctgctttgc cttctccatc agcaggc                         37

SEQ ID NO: 47          moltype = DNA   length = 30
FEATURE                Location/Qualifiers
misc_feature           1..30
                              note = Synthetic Oligonucleotide
source                 1..30
                              mol_type = other DNA
                              organism = synthetic construct
SEQUENCE: 47
gcctgctagt tctgctttgc cttctccatc                                 30

SEQ ID NO: 48          moltype = DNA   length = 37
FEATURE                Location/Qualifiers
misc_feature           1..37
                              note = Synthetic Oligonucleotide
source                 1..37
                              mol_type = other DNA
                              organism = synthetic construct
SEQUENCE: 48
gcctgctagt tctgctttgc cttctccatc agcaggc                         37

SEQ ID NO: 49          moltype = DNA   length = 30
FEATURE                Location/Qualifiers
misc_feature           1..30
                              note = Synthetic Oligonucleotide
```

-continued

```
source                  1..30
                        mol_type = other DNA
                        organism = synthetic construct
SEQUENCE: 49
gcctgctagt tctgctttgc cttctccatc                                    30

SEQ ID NO: 50           moltype = DNA   length = 37
FEATURE                 Location/Qualifiers
misc_feature            1..37
                        note = Synthetic Oligonucleotide
source                  1..37
                        mol_type = other DNA
                        organism = synthetic construct
SEQUENCE: 50
gcctgctagt tctgctttgc cttctccatc agcaggc                            37

SEQ ID NO: 51           moltype = DNA   length = 30
FEATURE                 Location/Qualifiers
misc_feature            1..30
                        note = Synthetic Oligonucleotide
source                  1..30
                        mol_type = other DNA
                        organism = synthetic construct
SEQUENCE: 51
gcctgctagt tctgctttgc cttctccatc                                    30

SEQ ID NO: 52           moltype = DNA   length = 38
FEATURE                 Location/Qualifiers
misc_feature            1..38
                        note = Synthetic Oligonucleotide
source                  1..38
                        mol_type = other DNA
                        organism = synthetic construct
SEQUENCE: 52
gcctgctagt tctgctttgc cttctccatc tagcaggc                           38

SEQ ID NO: 53           moltype = DNA   length = 30
FEATURE                 Location/Qualifiers
misc_feature            1..30
                        note = Synthetic Oligonucleotide
source                  1..30
                        mol_type = other DNA
                        organism = synthetic construct
SEQUENCE: 53
gcctgctagt tctgctttgc cttctccatc                                    30

SEQ ID NO: 54           moltype = DNA   length = 34
FEATURE                 Location/Qualifiers
misc_feature            1..34
                        note = Synthetic Oligonucleotide
source                  1..34
                        mol_type = other DNA
                        organism = synthetic construct
modified_base           21
                        mod_base = OTHER
                        note = uracil
SEQUENCE: 54
gcggagaagg caaagcagaa ttagcagtct ccgc                               34

SEQ ID NO: 55           moltype = DNA   length = 27
FEATURE                 Location/Qualifiers
misc_feature            1..27
                        note = Synthetic Oligonucleotide
source                  1..27
                        mol_type = other DNA
                        organism = synthetic construct
modified_base           21
                        mod_base = OTHER
                        note = uracil
SEQUENCE: 55
gcggagaagg caaagcagaa ttagcag                                       27

SEQ ID NO: 56           moltype = DNA   length = 34
FEATURE                 Location/Qualifiers
misc_feature            1..34
                        note = Synthetic Oligonucleotide
source                  1..34
                        mol_type = other DNA
                        organism = synthetic construct
```

-continued

```
modified_base        21
                     mod_base = OTHER
                     note = uracil
SEQUENCE: 56
gcggagaagg caaagcagaa ttagcagtct ccgc                              34

SEQ ID NO: 57        moltype = DNA   length = 27
FEATURE              Location/Qualifiers
misc_feature         1..27
                     note = Synthetic Oligonucleotide
source               1..27
                     mol_type = other DNA
                     organism = synthetic construct
modified_base        21
                     mod_base = OTHER
                     note = uracil
SEQUENCE: 57
gcggagaagg caaagcagaa ttagcag                                      27

SEQ ID NO: 58        moltype = DNA   length = 20
FEATURE              Location/Qualifiers
misc_feature         1..20
                     note = Synthetic Oligonucleotide
source               1..20
                     mol_type = other DNA
                     organism = synthetic construct
SEQUENCE: 58
tctttcccac craaccaaca                                              20

SEQ ID NO: 59        moltype = DNA   length = 29
FEATURE              Location/Qualifiers
misc_feature         1..29
                     note = Synthetic Oligonucleotide
source               1..29
                     mol_type = other DNA
                     organism = synthetic construct
SEQUENCE: 59
ctagttctgc tttgccttct ccatcttct                                    29

SEQ ID NO: 60        moltype = DNA   length = 24
FEATURE              Location/Qualifiers
misc_feature         1..24
                     note = Synthetic Oligonucleotide
source               1..24
                     mol_type = other DNA
                     organism = synthetic construct
SEQUENCE: 60
aagactccca ccgcagtttc agct                                         24

SEQ ID NO: 61        moltype = DNA   length = 24
FEATURE              Location/Qualifiers
misc_feature         1..24
                     note = Synthetic Oligonucleotide
source               1..24
                     mol_type = other DNA
                     organism = synthetic construct
SEQUENCE: 61
aagactccca ccgcagtttc agct                                         24

SEQ ID NO: 62        moltype = DNA   length = 24
FEATURE              Location/Qualifiers
misc_feature         1..24
                     note = Synthetic Oligonucleotide
source               1..24
                     mol_type = other DNA
                     organism = synthetic construct
SEQUENCE: 62
aagactccca ccgcagtttc agct                                         24

SEQ ID NO: 63        moltype = DNA   length = 29
FEATURE              Location/Qualifiers
misc_feature         1..29
                     note = Synthetic Oligonucleotide
source               1..29
                     mol_type = other DNA
                     organism = synthetic construct
SEQUENCE: 63
ctarttctgc tttgccttct ccatcttct                                    29
```

-continued

```
SEQ ID NO: 64         moltype = DNA   length = 29
FEATURE               Location/Qualifiers
misc_feature          1..29
                      note = Synthetic Oligonucleotide
source                1..29
                      mol_type = other DNA
                      organism = synthetic construct
SEQUENCE: 64
ctagttctgc tttgccttct ccatcttct                                29

SEQ ID NO: 65         moltype = DNA   length = 29
FEATURE               Location/Qualifiers
misc_feature          1..29
                      note = Synthetic Oligonucleotide
source                1..29
                      mol_type = other DNA
                      organism = synthetic construct
modified_base         7
                      mod_base = OTHER
                      note = uracil
modified_base         26..27
                      mod_base = OTHER
                      note = uracil
SEQUENCE: 65
agaagatgga gaaggcaaag cagaattag                                29

SEQ ID NO: 66         moltype = DNA   length = 29
FEATURE               Location/Qualifiers
misc_feature          1..29
                      note = Synthetic Oligonucleotide
source                1..29
                      mol_type = other DNA
                      organism = synthetic construct
modified_base         7
                      mod_base = OTHER
                      note = uracil
modified_base         27
                      mod_base = OTHER
                      note = uracil
SEQUENCE: 66
agaagatgga gaaggcaaag cagaactag                                29

SEQ ID NO: 67         moltype = DNA   length = 23
FEATURE               Location/Qualifiers
misc_feature          1..23
                      note = Synthetic Oligonucleotide
source                1..23
                      mol_type = other DNA
                      organism = synthetic construct
SEQUENCE: 67
gagacacaat tgcctacctg ctt                                      23

SEQ ID NO: 68         moltype = DNA   length = 26
FEATURE               Location/Qualifiers
misc_feature          1..26
                      note = Synthetic Oligonucleotide
source                1..26
                      mol_type = other DNA
                      organism = synthetic construct
modified_base         15
                      mod_base = OTHER
                      note = uracil
SEQUENCE: 68
gagtctaggt caaattcttt cccacc                                   26

SEQ ID NO: 69         moltype = DNA   length = 21
FEATURE               Location/Qualifiers
misc_feature          1..21
                      note = Synthetic Oligonucleotide
source                1..21
                      mol_type = other DNA
                      organism = synthetic construct
SEQUENCE: 69
ggtgctcttg accaaattgg g                                        21

SEQ ID NO: 70         moltype = DNA   length = 22
FEATURE               Location/Qualifiers
misc_feature          1..22
                      note = Synthetic Oligonucleotide
```

```
source                  1..22
                        mol_type = other DNA
                        organism = synthetic construct
SEQUENCE: 70
ctttcccacc raaccaacag tg                                              22

SEQ ID NO: 71           moltype = DNA   length = 29
FEATURE                 Location/Qualifiers
misc_feature            1..29
                        note = Synthetic Oligonucleotide
source                  1..29
                        mol_type = other DNA
                        organism = synthetic construct
SEQUENCE: 71
ttagtcatya cagtgactga caacaaagg                                       29

SEQ ID NO: 72           moltype = DNA   length = 23
FEATURE                 Location/Qualifiers
misc_feature            1..23
                        note = Synthetic Oligonucleotide
source                  1..23
                        mol_type = other DNA
                        organism = synthetic construct
SEQUENCE: 72
aggtaagctc cwagatctac tat                                             23

SEQ ID NO: 73           moltype = DNA   length = 23
FEATURE                 Location/Qualifiers
misc_feature            1..23
                        note = Synthetic Oligonucleotide
source                  1..23
                        mol_type = other DNA
                        organism = synthetic construct
SEQUENCE: 73
aggtaagctc cwagatctac tat                                             23

SEQ ID NO: 74           moltype = DNA   length = 23
FEATURE                 Location/Qualifiers
misc_feature            1..23
                        note = Synthetic Oligonucleotide
source                  1..23
                        mol_type = other DNA
                        organism = synthetic construct
SEQUENCE: 74
aggtaagctc ctagatctac tat                                             23

SEQ ID NO: 75           moltype = DNA   length = 32
FEATURE                 Location/Qualifiers
misc_feature            1..32
                        note = Synthetic Oligonucleotide
source                  1..32
                        mol_type = other DNA
                        organism = synthetic construct
modified_base           9
                        mod_base = OTHER
                        note = uracil
SEQUENCE: 75
ttagtcatta cagtgactga caacaaagga gc                                   32

SEQ ID NO: 76           moltype = DNA   length = 21
FEATURE                 Location/Qualifiers
misc_feature            1..21
                        note = Synthetic Oligonucleotide
source                  1..21
                        mol_type = other DNA
                        organism = synthetic construct
SEQUENCE: 76
tagaccatgt gaattccctg c                                               21

SEQ ID NO: 77           moltype = DNA   length = 29
FEATURE                 Location/Qualifiers
misc_feature            1..29
                        note = Synthetic Oligonucleotide
source                  1..29
                        mol_type = other DNA
                        organism = synthetic construct
SEQUENCE: 77
ttagtcatya cagtgactga caacaaagg                                       29
```

```
SEQ ID NO: 78            moltype = DNA  length = 29
FEATURE                  Location/Qualifiers
misc_feature             1..29
                         note = Synthetic Oligonucleotide
source                   1..29
                         mol_type = other DNA
                         organism = synthetic construct
modified_base            9
                         mod_base = OTHER
                         note = uracil
SEQUENCE: 78
ttagtcatta cagtgactga caacaaagg                                    29

SEQ ID NO: 79            moltype = DNA  length = 26
FEATURE                  Location/Qualifiers
misc_feature             1..26
                         note = Synthetic Oligonucleotide
source                   1..26
                         mol_type = other DNA
                         organism = synthetic construct
SEQUENCE: 79
acaaatgcaa aaatcatacc ttactc                                       26

SEQ ID NO: 80            moltype = DNA  length = 36
FEATURE                  Location/Qualifiers
misc_feature             1..36
                         note = Synthetic Oligonucleotide
source                   1..36
                         mol_type = other DNA
                         organism = synthetic construct
SEQUENCE: 80
cgtggcttta tgtatttgaa tgctcctttg gccacg                            36

SEQ ID NO: 81            moltype = DNA  length = 30
FEATURE                  Location/Qualifiers
misc_feature             1..30
                         note = Synthetic Oligonucleotide
source                   1..30
                         mol_type = other DNA
                         organism = synthetic construct
SEQUENCE: 81
cgtggcttta tgtatttgaa tgctcctttg                                   30

SEQ ID NO: 82            moltype = DNA  length = 36
FEATURE                  Location/Qualifiers
misc_feature             1..36
                         note = Synthetic Oligonucleotide
source                   1..36
                         mol_type = other DNA
                         organism = synthetic construct
SEQUENCE: 82
cgtggcttta tgtatttgaa tgctcctttg gccacg                            36

SEQ ID NO: 83            moltype = DNA  length = 30
FEATURE                  Location/Qualifiers
misc_feature             1..30
                         note = Synthetic Oligonucleotide
source                   1..30
                         mol_type = other DNA
                         organism = synthetic construct
SEQUENCE: 83
cgtggcttta tgtatttgaa tgctcctttg                                   30

SEQ ID NO: 84            moltype = DNA  length = 38
FEATURE                  Location/Qualifiers
misc_feature             1..38
                         note = Synthetic Oligonucleotide
source                   1..38
                         mol_type = other DNA
                         organism = synthetic construct
SEQUENCE: 84
cggtggcttt atgtatttga atgctccttt ggccaccg                          38

SEQ ID NO: 85            moltype = DNA  length = 31
FEATURE                  Location/Qualifiers
misc_feature             1..31
                         note = Synthetic Oligonucleotide
source                   1..31
                         mol_type = other DNA
```

-continued

```
                                    organism = synthetic construct
SEQUENCE: 85
cggtggcttt atgtatttga atgctccttt g                                          31

SEQ ID NO: 86          moltype = DNA   length = 39
FEATURE                Location/Qualifiers
misc_feature           1..39
                       note = Synthetic Oligonucleotide
source                 1..39
                       mol_type = other DNA
                       organism = synthetic construct
SEQUENCE: 86
cggtggcttt atgtatttga atgctccttt gagccaccg                                  39

SEQ ID NO: 87          moltype = DNA   length = 31
FEATURE                Location/Qualifiers
misc_feature           1..31
                       note = Synthetic Oligonucleotide
source                 1..31
                       mol_type = other DNA
                       organism = synthetic construct
SEQUENCE: 87
cggtggcttt atgtatttga atgctccttt g                                          31

SEQ ID NO: 88          moltype = DNA   length = 26
FEATURE                Location/Qualifiers
misc_feature           1..26
                       note = Synthetic Oligonucleotide
source                 1..26
                       mol_type = other DNA
                       organism = synthetic construct
SEQUENCE: 88
acaaatgcaa aaatcatacc ttactc                                                26

SEQ ID NO: 89          moltype = DNA   length = 29
FEATURE                Location/Qualifiers
misc_feature           1..29
                       note = Synthetic Oligonucleotide
source                 1..29
                       mol_type = other DNA
                       organism = synthetic construct
SEQUENCE: 89
ttagtcatta cagtgactga caacaaagg                                             29

SEQ ID NO: 90          moltype = DNA   length = 29
FEATURE                Location/Qualifiers
misc_feature           1..29
                       note = Synthetic Oligonucleotide
source                 1..29
                       mol_type = other DNA
                       organism = synthetic construct
SEQUENCE: 90
ttagtcatya cagtgactga caacaaagg                                             29

SEQ ID NO: 91          moltype = DNA   length = 29
FEATURE                Location/Qualifiers
misc_feature           1..29
                       note = Synthetic Oligonucleotide
source                 1..29
                       mol_type = other DNA
                       organism = synthetic construct
modified_base          9
                       mod_base = OTHER
                       note = uracil
SEQUENCE: 91
ttagtcatta cagtgactga caacaaagg                                             29

SEQ ID NO: 92          moltype = DNA   length = 23
FEATURE                Location/Qualifiers
misc_feature           1..23
                       note = Synthetic Oligonucleotide
source                 1..23
                       mol_type = other DNA
                       organism = synthetic construct
SEQUENCE: 92
aggtaagctc cgagatctac tat                                                   23

SEQ ID NO: 93          moltype = DNA   length = 25
FEATURE                Location/Qualifiers
```

```
misc_feature             1..25
                         note = Synthetic Oligonucleotide
source                   1..25
                         mol_type = other DNA
                         organism = synthetic construct
SEQUENCE: 93
ctaggtaagc tccaagatct actat                                              25

SEQ ID NO: 94            moltype = DNA  length = 25
FEATURE                  Location/Qualifiers
misc_feature             1..25
                         note = Synthetic Oligonucleotide
source                   1..25
                         mol_type = other DNA
                         organism = synthetic construct
SEQUENCE: 94
ctaggtaagc tccaagatct actat                                              25

SEQ ID NO: 95            moltype = DNA  length = 25
FEATURE                  Location/Qualifiers
misc_feature             1..25
                         note = Synthetic Oligonucleotide
source                   1..25
                         mol_type = other DNA
                         organism = synthetic construct
SEQUENCE: 95
ctaggtaagc tcctagatct actat                                              25

SEQ ID NO: 96            moltype = DNA  length = 25
FEATURE                  Location/Qualifiers
misc_feature             1..25
                         note = Synthetic Oligonucleotide
source                   1..25
                         mol_type = other DNA
                         organism = synthetic construct
SEQUENCE: 96
ctaggtaagc tcctagatct actat                                              25

SEQ ID NO: 97            moltype = RNA  length = 29
FEATURE                  Location/Qualifiers
source                   1..29
                         mol_type = other RNA
                         organism = synthetic construct
SEQUENCE: 97
cctttgttgt cagtcactgt gatgactaa                                          29

SEQ ID NO: 98            moltype = RNA  length = 29
FEATURE                  Location/Qualifiers
source                   1..29
                         mol_type = other RNA
                         organism = synthetic construct
SEQUENCE: 98
cctttgttgt cagtcactgt aatgactaa                                          29

SEQ ID NO: 99            moltype = DNA  length = 21
FEATURE                  Location/Qualifiers
misc_feature             1..21
                         note = Synthetic Oligonucleotide
source                   1..21
                         mol_type = other DNA
                         organism = synthetic construct
SEQUENCE: 99
tgaagttgat gaacaaagtg g                                                  21

SEQ ID NO: 100           moltype = DNA  length = 23
FEATURE                  Location/Qualifiers
misc_feature             1..23
                         note = Synthetic Oligonucleotide
source                   1..23
                         mol_type = other DNA
                         organism = synthetic construct
SEQUENCE: 100
gatgatgatc cygcatcact aac                                                23

SEQ ID NO: 101           moltype = DNA  length = 23
FEATURE                  Location/Qualifiers
misc_feature             1..23
                         note = Synthetic Oligonucleotide
source                   1..23
```

-continued

```
                            mol_type = other DNA
                            organism = synthetic construct
modified_base               12
                            mod_base = OTHER
                            note = uracil
SEQUENCE: 101
gatgatgatc ctgcatcact aac                                                    23

SEQ ID NO: 102              moltype = DNA   length = 26
FEATURE                     Location/Qualifiers
misc_feature                1..26
                            note = Synthetic Oligonucleotide
source                      1..26
                            mol_type = other DNA
                            organism = synthetic construct
SEQUENCE: 102
atgggtgcct atgttccagt catctg                                                 26

SEQ ID NO: 103              moltype = DNA   length = 21
FEATURE                     Location/Qualifiers
misc_feature                1..21
                            note = Synthetic Oligonucleotide
source                      1..21
                            mol_type = other DNA
                            organism = synthetic construct
SEQUENCE: 103
caccagccct caataccacc c                                                      21

SEQ ID NO: 104              moltype = DNA   length = 19
FEATURE                     Location/Qualifiers
misc_feature                1..19
                            note = Synthetic Oligonucleotide
source                      1..19
                            mol_type = other DNA
                            organism = synthetic construct
SEQUENCE: 104
gcttcaatgg tccacagtt                                                         19

SEQ ID NO: 105              moltype = DNA   length = 19
FEATURE                     Location/Qualifiers
misc_feature                1..19
                            note = Synthetic Oligonucleotide
source                      1..19
                            mol_type = other DNA
                            organism = synthetic construct
SEQUENCE: 105
gcttcaatgg tccacagtt                                                         19

SEQ ID NO: 106              moltype = DNA   length = 23
FEATURE                     Location/Qualifiers
misc_feature                1..23
                            note = Synthetic Oligonucleotide
source                      1..23
                            mol_type = other DNA
                            organism = synthetic construct
modified_base               12
                            mod_base = OTHER
                            note = uracil
SEQUENCE: 106
gatgatgatc ctgcatcact aac                                                    23

SEQ ID NO: 107              moltype = DNA   length = 34
FEATURE                     Location/Qualifiers
misc_feature                1..34
                            note = Synthetic Oligonucleotide
source                      1..34
                            mol_type = other DNA
                            organism = synthetic construct
SEQUENCE: 107
cgctgctggc acagatgact ggaacatagc agcg                                        34

SEQ ID NO: 108              moltype = DNA   length = 28
FEATURE                     Location/Qualifiers
misc_feature                1..28
                            note = Synthetic Oligonucleotide
source                      1..28
                            mol_type = other DNA
                            organism = synthetic construct
SEQUENCE: 108
```

```
cgctgctggc acagatgact ggaacata                                          28

SEQ ID NO: 109              moltype = DNA   length = 36
FEATURE                     Location/Qualifiers
misc_feature                1..36
                            note = Synthetic Oligonucleotide
source                      1..36
                            mol_type = other DNA
                            organism = synthetic construct
SEQUENCE: 109
ccgagcaagt ctgctggcac agatgactgg gctcgg                                 36

SEQ ID NO: 110              moltype = DNA   length = 30
FEATURE                     Location/Qualifiers
misc_feature                1..30
                            note = Synthetic Oligonucleotide
source                      1..30
                            mol_type = other DNA
                            organism = synthetic construct
SEQUENCE: 110
ccgagcaagt ctgctggcac agatgactgg                                        30

SEQ ID NO: 111              moltype = DNA   length = 38
FEATURE                     Location/Qualifiers
misc_feature                1..38
                            note = Synthetic Oligonucleotide
source                      1..38
                            mol_type = other DNA
                            organism = synthetic construct
SEQUENCE: 111
ccgagcaagt ctgctggcac agatgactgg ttgctcgg                               38

SEQ ID NO: 112              moltype = DNA   length = 30
FEATURE                     Location/Qualifiers
misc_feature                1..30
                            note = Synthetic Oligonucleotide
source                      1..30
                            mol_type = other DNA
                            organism = synthetic construct
SEQUENCE: 112
ccgagcaagt ctgctggcac agatgactgg                                        30

SEQ ID NO: 113              moltype = DNA   length = 33
FEATURE                     Location/Qualifiers
misc_feature                1..33
                            note = Synthetic Oligonucleotide
source                      1..33
                            mol_type = other DNA
                            organism = synthetic construct
SEQUENCE: 113
cgccagtcat ctgtgccagc agacttgctg gcg                                    33

SEQ ID NO: 114              moltype = DNA   length = 27
FEATURE                     Location/Qualifiers
misc_feature                1..27
                            note = Synthetic Oligonucleotide
source                      1..27
                            mol_type = other DNA
                            organism = synthetic construct
SEQUENCE: 114
cgccagtcat ctgtgccagc agacttg                                           27

SEQ ID NO: 115              moltype = DNA   length = 24
FEATURE                     Location/Qualifiers
misc_feature                1..24
                            note = Synthetic Oligonucleotide
source                      1..24
                            mol_type = other DNA
                            organism = synthetic construct
SEQUENCE: 115
tagtatgttg atgcttgcaa gttc                                              24

SEQ ID NO: 116              moltype = DNA   length = 984
FEATURE                     Location/Qualifiers
source                      1..984
                            mol_type = genomic DNA
                            organism = Influenza A virus
SEQUENCE: 116
atgagtcttc taaccgaggt cgaaacgtac gttctttcta tcataccgtc aggccccctc    60
```

```
aaagccgaga tcgcgcagag actggaaagt gtctttgcag gaaagaacac agatcttgag  120
gctctcatgg aatggctaaa gacaagacca atcttgtcac ctctgactaa gggaatttta  180
ggatttgtgt tcacgctcac cgtgcccagt gagcgaggac tgcagcgtag acgctttgtc  240
caaaatgccc tgaatgggaa tggggaccca aacaacatgg atagagcagt taaactatac  300
aagaagctca aaagagaaat aacgttccat ggggccaaag aggtgtcact aagctattca  360
actggtgcac ttgccagttg catgggcctc atatacaaca ggatgggaac agtgaccaca  420
gaagctgctt ttggtctagt gtgtgccact tgtgaacaga ttgctgattc acagcatcgg  480
tctcacagac agatggctac aaccaccaat ccactaatca ggcatgagaa cagaatggtg  540
ctggctagca ctacggcaaa ggctatggaa cagatggctg gatcgagtga acaggcagcg  600
gaggccatgg aggttgctaa tcagactagg cagatggtac atgcaatgag aactattggg  660
actcatccta gctccagtac gggtctgaaa gatgaccttc ttgaaaattt gcaggcctac  720
cagaagcgaa tgggagtgca gatgcagcga ttcaagtgat cttctcgcca ttgcagcaaa  780
tatcattggg atcttgcacc tgatattgtg gattactgat cgtctttttt tcaaatgtat  840
ttatcgtcgc tttaaatacg gtttgaaaag agggccttct acggaaggag ggcctgagtc  900
catgagggaa gaatatcaac aggaacagca gagtgctgtg gatgttgacg atggtcattt  960
tgtcaacata gagctagagt aaaa                                          984

SEQ ID NO: 117          moltype = DNA  length = 1076
FEATURE                 Location/Qualifiers
source                  1..1076
                        mol_type = genomic DNA
                        organism = Influenza B virus
SEQUENCE: 117
atgtcgctgt ttggagacac aattgcctac ctgctttcat tgacagaaga tggagaaggc  60
aaagcagaac tagcagaaaa attacactgt tggttcggtg ggaaagaatt tgacctagac  120
tctgccttgg aatggataaa aaacaaaaga tgcttaactg atatacagaa agcactaatt  180
ggtgcatcta tctgcttttt aaaacccaaa gaccaggaaa gaaaaagaag attcatcaca  240
gagcccctat caggaatggg aacaacagca acaaaaaaga agggcctgat tctagctgag  300
agaaaaatga gaaaatgtgt gagcttccat gaagcatttg aaatagcaga aggccatgaa  360
agctcagcgt tactgtattg tctcatggtc atgtacctga tcctggaaa ttattcaatg  420
caagtaaaac taggaacgct ctgtgctttg tgcgagaaac aagcatcaca ttcacacagg  480
gctcatagca gagcagcgag atcttcagtc cccggagtga gacgagaaat gcagatggtc  540
tcagctatga acacagcaaa aacaatgaat ggaatgggaa aggagaaga cgtccaaaaa  600
ctggcagaag aactgcaaag caacattgga gtattgagat ctctgggggc aagccaaaag  660
aatggggaag gaattgcaaa ggatgtaatg caagtgctaa agcagagctc tatgggaaat  720
tcagctcttg tgaagaaata cctataatgc tcgaaccatt tcagattctt tcaatttgtt  780
ctttatttt atcagctctc catttcatgg cctggacaat aggacatttg aatcaaataa  840
aaagaggagt aaacatgaaa atacgaataa aggggcaaa taaagagacg ataaacagag  900
aggtatcaat tttgagacac aattaccaaa aagaaattca ggctaaagaa gcaatgaagg  960
aagtactctc tgacaacatg gaggtattga gtgaccacat agtaattgag gggctttctg  1020
cagaagagat aataaaaatg ggtgaaacag ttttggaggt agaaaaatcg cattaa       1076

SEQ ID NO: 118          moltype = DNA  length = 15226
FEATURE                 Location/Qualifiers
source                  1..15226
                        mol_type = genomic DNA
                        organism = respiratory syncytial virus
SEQUENCE: 118
acgcgaaaaa atgcgtacaa caaacttgcg taaaccaaaa aaatgggca aataagaatt    60
tgataagtac cacttaaatt taactccctt ggttagagat gggcagcaat cgttgagta   120
tgataaaagt tagattacaa aatttgtttg acaatgatga agtagcattg ttaaaaataa  180
catgctatac tgacaaatta atacatttaa ctaatgcttt ggctaaggca gtgatacata  240
caatcaaatt gaatggcatt gtgtttgtgc atgttattac aagtagtgat atttgcccta  300
ataataatat tgtagtaaaa tccaatttca caacaatgcc agtgctacaa aatggaggtt  360
atatatggga aatgatggaa ttaacacatt gctctcaacc taatggtcta atagatgaca  420
attgtgaaat taaattctcc aaaaaactaa gtgattcaac aatgaccaat tatatgaatc  480
aattatctga attacttgga tttgatctta atccataaat tataattaat atcaactagc  540
aaatcaatgt cactagcacc attagttaat ataaaactta acagaagaca aaaatggggc  600
aaataaatca actcagccaa cccaaccatg gacacaaccc acaatgatac cacaccacaa  660
agactgatga tcacagacat gagaccgttg tcacttgaga ctacaataac atcactaacc  720
agagacatca taacacacag atttatatac ttaataaaatc atgaatgcat agtgagaaaa  780
cttgatgaaa gacaggccac atttacattc ctggtcaact atgaaatgaa actattgcac  840
aaagtaggaa gcactaaata taaaaaatat actgaataca acacaaaata tggcactttc  900
cctatgccga tattcatcaa tcatgatggg ttcttagaat gcattggcat taagtcctac  960
aagcatactc ccataatata caagtatgat ctcaatccat gaatttcaac acaagattca  1020
cacaatccaa aacaacaact ttatgcataa ctacactcca tagtccaaat gggagcctga  1080
aattatagta atttaaaatt aaggagagac ataagataga agatggggca aatacaaaga  1140
tggctcttag caaagtcaag ttgaatgata cactcaacaa agatcaactt ctgtcatcta  1200
gcaaatacac catccaacgg agcacaggag atagtattga tactcctaat tatgatgtgc  1260
agaaacacat caataagtta tgtggcatgt tattaatcac agaagatgct aatcataaat  1320
tcactgggtt aataggtatg ttatatgcta tgtctaggtt aggaagagaa gacaccataa  1380
aaatactcag agatgcggga tatcatgtaa aagcaaatgg agtagatgta acaacacatc  1440
gtcaagacat caatgggaaa gaaatgaaat ttgaagtgtt aacattggca agcttaacaa  1500
ctgaaaattca aatcaacatt gagatagaat ctagaaaatc ctacaaaaaa atgctaaaag  1560
aaatgggaga ggtagctcca gaatacaggc atgattctcc tgattgtggg atgataaat   1620
tatgtatagc agcattagta ataaccaaat tggcagcagg ggatagatct ggtcttacag  1680
ccgtgattag gagagctaat aatgtcctaa aaaatgaaat gaaacgttac aaaaggcttac  1740
tacccaagga tatagccaac agcttctatg aagtgtttga aaaacatccc cactttatag  1800
atgtttttgt tcattttggt atagcacaat cttccaccag aggtggcagt agagttgaag  1860
```

-continued

```
ggatttttgc aggattgttt atgaatgcct atggtgcagg gcaagtaatg ctacggtggg   1920
gagtcttagc aaaatcagtt aaaaatatta tgttaggaca tgctagtgtg caagcagaaa   1980
tggaacaagt tgttgaggtt tatgaatatg cccaaaaatt gggtggagaa gcaggattct   2040
accatatatt gaacaaccca aaagcatcat tattatcttt gactcaattt cctcactttt   2100
ccagtgtagt attaggcaat gctgctggcc taggcataat gggagagtac agaggtacac   2160
cgaggaatca agatctatat gatgcagcaa aggcatatgc tgaacaactc aaagaaaatg   2220
gtgtgattaa ctacagtgta ttagacttga cagcagaaga actagaggct atcaaacatc   2280
agcttaatcc aaaagataat gatgtagagc tttgagttaa taaaaaatgg ggcaaataaa   2340
tcatcatgga aaagtttgct cctgaattcc atggagaaga tgcaaacaac agggctacta   2400
aattcctaga atcaataaag ggcaaattca catcacctaa agatcccaag aaaaaagata   2460
gtatcatatc tgtcaactca atagatatag aagtaaccaa agaaagccct ataacatcaa   2520
attcaaccat tattaaccca acaaatgaga cagatgataa tgcagggaac aagcccaatt   2580
atcaaagaaa acctctagta agtttcaaag aagaccctat accaagtgat aatccctttt   2640
caaaactata caaagaaacc atagagacat ttgataacaa tgaagaagaa tctagctatt   2700
catatgaaga aataaatgat cagacgaacg ataatataac tgcaagatta gataggattg   2760
atgaaaaatt aagtgaaata ctaggaatgc ttcacacatt agtagtagca agtgcaggac   2820
ctacatctgc tagggatggt ataagagatg ccatggttgg tttaagagaa gaaatgatag   2880
aaaaaatcag aactgaagca ttaatgacca atgacagatt agaagctatg gcaagactca   2940
ggaatgagga aagtgaaaag atggcaaaag acacatcaga tgaagtgtct ctcaatccaa   3000
catcagagaa attgaacaac ctgttggaag ggaatgatag tgacaatgat ctatcacttg   3060
aagatttctg attagttaca aatctgcact tcaacacaca acaccaacag aagaccaaca   3120
aacaaaccaa cccactcatc caaccaaaca tccatccgcc aatcagccaa acagccaaca   3180
aaacaaccag ccaatccaaa accagccacc tggaaaaaat cgacaatata gttacaaaaa   3240
aagaaaaggg tggggcaaat atggaaacat acgtgaacaa gcttcacgaa ggctccacat   3300
acacagctgc tgttcaatac aatgtcctag aaaaagacga tgaccctgca tcacttacaa   3360
tatgggtgcc catgttccaa tcatctatgc cagcagattt acttataaaa gaactagcta   3420
atgtcaacat actagtgaaa caaatatcca cacccaaggg accttcacta agagtcatga   3480
taaactcaag aagtgcattg ctagcacaaa tgcccagcaa atttaccata tgtgctaatg   3540
tgtccttgga tgaagaagc aaactggcat atgatgtaac cacaccctgt gaaatcaagg   3600
catgtagtct aacatgccta aaatcaaaaa atatgttaac tacagttaaa gatctcacta   3660
tgaagacact caaccccaca catgatatta ttgctttatg tgaatttgaa aacatagtaa   3720
catcaaaaaa agtcataata ccaacatacc taagatccat cagtgtcaga aataaagatc   3780
tgaacacact tgaaaatata acaaccactg aattcaaaaa tgccatcaca aatgcaaaaa   3840
tcatccctta ctcaggatta ctattagtca tcacagtgac tgacaacaaa ggagcattca   3900
aatacataaa gccgcaaagt caattcatag tagatcttgg agcttaccta gaaaaagaaa   3960
gtatatatta tgttaccaca aattggaagc acacagctac acgatttgca atcaaaccca   4020
tggaagatta accttttttcc tccacatcag tgagtcaatt catacaaact ttctacctac   4080
attcttcact tcaccattac aatcacaaac actctgtggt tcaaccaatc aaacaaaact   4140
tatctgaagt ctcagatcat cccaagtcat tgttcatcag atctagtaat caaataagtt   4200
aataaaaata tacacatggg gcaaataatc atcggaggaa atccaactaa tcacaatatc   4260
tgttaacata gacaagtcaa cacaccagac agaatcaacc aatggaaaat acatccataa   4320
caatagaatt ctcaagcaaa ttctggcctt actttacact aatacacatg atcacaacaa   4380
taatctcttt gctaatcata atctccatca tgactgcaat acataacaaa ctttgtgaat   4440
ataacgtatt ccataacaaa acctttgagt taccaagagc tcgagtcaac acatagcatt   4500
catcaatcta atagctcaaa atagtaacct tgcatttaaa agtgaacaac ccccacctct   4560
ttacaacacc tcattaacat cccaccatgc aaaccaccat ccatactata aagtagttaa   4620
ttaaaaatag tcataacaat gaactaggat atcaagacta acaataacgt tggggcaaat   4680
gcaaacatgt ccaaaaacaa ggaccaacgc accgctaaga cactagaaaa gacctgggac   4740
actctcaatc atttattatt catatcatcg ggcttatata agttaaatct taaatctata   4800
gcacaaatca cattatccat tctggcaatg ataatctcaa cttcacttat aattacagcc   4860
atcatattca tagcctcggc aaaccacaaa gtcacactaa caactgcaat catacaagat   4920
gcaacaagcc agatcaagaa cacaacccca acatacctca ctcaggatcc tcagcttgga   4980
atcagcttct ccaatctgtc tgaaattaca tcacaaacca ccaccatact agcttcaaca   5040
acaccaggag tcaagtcaaa cctgcaaccc acaacagtca agactaaaaa cacaacaaca   5100
acccaaacac aacccagcaa gcccactaca aaacaacgcc aaaacaaacc accaaacaaa   5160
cccaataatg attttcactt cgaagtgttt aactttgtac cctgcagcat atgcagcaac   5220
aatccaacct gctgggctat ctgcaaaaga ataccaaaca aaaaccagg aaagaaaacc   5280
accaccaagc ctacaaaaaa accaaccttc aagacaacca aaaaagatct caaacctcaa   5340
accactaaac caaaggaagt acccaccacc aagcccacag aagagccaac catcaacacc   5400
accaaaacaa acatcacaac tacactgctc accaacaaca ccacaggaaa tccaaaactc   5460
acaagtcaaa tggaaacctt ccactcaacc tcctccgaag gcaatctaag cccttctcaa   5520
gtctccacaa catccgagca cccatcacaa ccctcatctc cacccaacac aacacgccag   5580
tagttattaa aaaacatatt atcacaaaag gccatgacca actcaaacag aatcaaaata   5640
aactctgggg caaataacaa tggagttgcc aatcctcaaa acaaatgcaa ttaccacaat   5700
cctcgctgca gtcacatttt gctttgcttc tagtcaaaac atcactgaag aatttttatca   5760
atcaacatgc agtgcagtta gcaaaggcta tcttagtgct ctaagaactg ttggtatac   5820
tagtgttata actatagaat taagtaatat caaggaaaat aagtgtaatg aacagatgc   5880
taaggtaaaa ttgataaacc aagaattaga taaatataaa aatgctgtaa cagaattgca   5940
gttgctcatg caaagcacaa cagcagcaaa caatcgagcc agaagagaac taccaaggtt   6000
tatgaattat acactcaaca ataccaaaaa aaccaatgta acattaagca agaaaaggaa   6060
aagaagattc cttggttttt tgttaggtgt tggatctgca atcgccagtg gcattgctgt   6120
atctaaggtc ctgcacttag aaggagaagt gaacaagatc aaaagtgctc tactatccac   6180
aaacaaggcc gtagtcagct tatcaaatgg agttagtgtc ttaaccagca aagtgttaga   6240
cctcaaaaac tatatagata aacaattgtt acctattgtg aataagcaaa gctgcagaat   6300
atcaaatata gaaactgtga tagagttcca acaaaagaac aacagactac tagagattac   6360
caggggaattt agtgttaatg caggtgtaac tacacctgta agcacttaca tgttaactaa   6420
tagtgaattattg ttgtcattaa tcaatgatat gcctataaca aatgatcaga aaaagttaat   6480
gtccaacaat gttcaaatag ttagacagca aagttactct atcatgtcca taataaaaga   6540
ggaagtctta gcatatgtag tacaattacc actatatggt gtgatagata cacccttgttg   6600
```

-continued

```
gaaattacac acatcccctc tatgtacaac caacacaaaa gaagggtcaa acatctgttt   6660
aacaagaact gacagaggat ggtactgtga caatgcagga tcagtatctt tcttcccaca   6720
agctgaaaca tgtaaagttc aatcgaatcg agtattttgt gacacaatga acagtttaac   6780
attaccaagt gaagtaaatc tctgcaatgt tgacatattc aatcccaaat atgattgtaa   6840
aattatgact tcaaaaacag atgtaagcag ctccgttatc acatctctag gagccattgt   6900
gtcatgctat ggcaaaacta aatgtacagc atccaataaa aatcgtggaa tcataaaagac  6960
attttctaac gggtgtgatt atgtatcaaa taaaggggtg gacactgtgt ctgtaggtaa   7020
cacattatat tatgtaaata agcaagaagg caaaagtctc tatgtaaaag gtgaaccaat   7080
aataaatttc tatgacccat tagtattccc ctctgatgaa tttgatgcat caatatctca   7140
agtcaatgag aagattaacc agagtttagc atttattcgt aaatccgatg aattattaca   7200
tcatgtaaat gctggtaaat caaccacaaa tatcatgata actactataa ttatagtgat   7260
tatagtaata ttgttatcat taattgctgt tggactgctc ctatactgta aggccagaag   7320
cacaccagtc acactaagca aggatcaact gagtggtata aataatattg catttagtaa   7380
ctgaataaaa atagcaccta atcatgttct tacaatggtt tactatctgc tcatagacaa   7440
cccatctatc attggatttt cttaaaatct gaacttcatc gaaactctta tctataaacc   7500
atctcactta cactatttaa gtagattcct agtttatagt tatataaaac acaattgaat   7560
accagattaa cttactatct gtaaaaatga gaactggggc aaatatgtca cgaaggaatc   7620
cttgcaaatt tgaaattcga ggtcattgct tgaatggtaa ggagatgtcat tttagtcata  7680
attattttga atggccaccc catgcactgc tcgtaagaca aaactttatg ttaaacagaa   7740
tacttaagtc tatggataaa agtatagata ccttatcaga aataagtgga gctgcagagt   7800
tggacagaac agaagagtat gctcttggtg tagttggagt gctagagagt tatataggat   7860
caataaataa tataactaaa caatcagcat gtgttgccat gagcaaactc ctcactgaac   7920
tcaatagtga tgatatcaaa aaactgagag acaatgaaga gctaaattca cccaagataa   7980
gagtgtacaa tactgtcata tcatatattg aaagcaacag gaaaaacaat aaacaaacta   8040
tccatctgtt aaaaagattg ccagcagacg tattgaagaa aaccatcaaa aacacattgg   8100
atatccacaca gagcataacc atcaacaacc caaaagaatt aactgttagt gatacaaaatg   8160
accatgccaa aaataatgat actacctgac aaatatcctt gtagtataac ttccatacta   8220
ataacaagta gatgtagagt cactatgtat aatcgaaaga acacactata tttcaatcaa   8280
aacaacccaa ataaccatat gtactcaccg aatcaaacat tcaatgaaat ccattggacc   8340
tcacaagact tgattgacac aattcaaaat tttctacagc atctaggtgt tattgaggat   8400
atatatacaa tatatatatt agtgtcataa cactcaatcc taatactgac catatcgttg   8460
aattattaat tcaaataatt caagctgtgg gacaaaatgg atcccattat taatggaaat   8520
tctgctaatg tttatctaac cgatagttat ttaaaaggtg ttatctcttt ctcagagtgt   8580
aatgctttag gaagttacat attcaatggt ccttatctca aaatgatta taccaactta   8640
attagtagac aaaatccatt aatagaacac atgaatctaa agaaactaaa tataacacag   8700
tccttaatat ctaagtatca taaaggtgaa ataaaattag aagagcctac ttattttcag   8760
tcattactta tgacatacaa gagtatgacc tcgttggaac agattgctac cactaattta   8820
cttaaaaaga taataagaag agctatagaa ataagtgatg tcaaagtcta tgctatattg   8880
aataaactag ggcttaaaga aaaggacaag attaaatcca acaatggaca ggatgaagac   8940
aactcagtta ttacgaccat aatcaaagat gatatacttt cagctgttaa ggataatcaa   9000
tctcatctta aagcagacaa aaatcactct acaaaacaaa aagacacaat caaaacaaca   9060
ctcttgaaga aattaatgtg ttcaatgcag catcctccat catggttaat acattggttt   9120
aatttataca caaaattaaa caacatatta acacagtatc gatcaaatga ggttaaaaac   9180
catgggttta tattgataga taatcaaact cttagtggat ttcaatttat tttgaatcaa   9240
tatgttgta tagtttatca taaggaactc aaaagaatta ctgtgacaac ctataatcaa   9300
ttcttgacat ggaaagatat tagccttagt agattaaatg tttgtttaat tacatggatt   9360
agtaactgct tgaacacatt aaataaaagc ttaggcttaa gatgcggatt caataatgtt   9420
atcttgacac aactattcct ttatggtgat tgtatactaa agctatttca caatgagggg   9480
ttctacataa taaaagaggt agagggatt attatgtctc taattttaaa tataacagaa   9540
gaagatcaat tcagaaaacg attttataat agtatgctca acaacatcac agatgctgct   9600
aataaagctc agaaaaatct gctatcaaga gtatgtcata cattattaga taagacagta   9660
tccgataata taataaatgg cagatggata attctattaga gtaagttcct taaattaatt   9720
aagcttgcag gtgacaataa ccttaacaat ctgagtgaac tatatttttt gttcagaata   9780
tttgacacc caatggtaga tgaaagacaa gccatggatg ctgttaaagt taattgcaat   9840
gagaccaaat tttacttgtt aagcagtttg agtatgttaa gaggtgcctt tatatataga   9900
attataaaag ggtttgtaaa taattacaac agatggccta ctttaagaaa tgctattgtt   9960
ttaccttaa gatggttaac ttactataaa ctaaacactt atccttcttt gttggaactt   10020
acagaaagag atttgattgt gttatcagga ctacgtttct atcgtgagtt tcggttgcct   10080
aaaaaagtgg atcttgaaat gattataaat gataaagcta tcacccccc taaaaatttg   10140
atatggacta gtttccctag aaattatatg ccgtcacaca tacaaaacta tatagaacat   10200
gaaaaattaa aattttccga gagtgataaa tcaagaagag tattagagta ttatttaaga   10260
gataacaaat tcaatgaatg tgatttatac aactgtgtag ttaatcaaag ttatctcaac   10320
aaccctaatc atgtggtatc attgacaggc aaagaaagag aactcagtgt aggtagaatg   10380
tttgcaatgc aaccgggaat gttcagacag gttcaaatat tggcagagaa aatgatagct   10440
gaaacatttt acaattctt tcctgaaagt cttacaagat atggtgatct agaactacaa   10500
aaaatattag aattgaaagc aggaataagt aacaaatcaa atcgctacaa tgataattac   10560
aacaattaca ttagtaagtg ctctatcatc acagatctca gcaaattcaa tcaagcattt   10620
cgatatgaaa cgtcatgtat ttgtagtgat gtgctggatg aactgcatgg tgtacaatct   10680
ctatttttcct ggttacattt aactattcct catgtcacaa taatatgcac atataggcat   10740
gcacccccct atataagaga tcatattgta gatcttaaca atgtagatga acaaagtgga   10800
ttatatagat atcacatggg tggtattgaa gggtggtgtc aaaaactatg gaccatagaa   10860
gctatatcac tattggatct aatatctctc aaagggaaat tctcaattac tgctttaatt   10920
aatggtgaca atcaatcaat agatataagc aaaccagtca gactcatgga aggtcaaact   10980
catgctcaag cagattattt gctagcatta aatagcctta aattactgta taaagagtat   11040
gcaggcatag gtcacaaatt aaaaggaact gagacttata tatcacgaga tatgcaattt   11100
atgagtaaaa caattcaaca taacggtgta tattaccctg ctagtataaa gaaagtccta   11160
agagtgggac cgtggataaa cactatactt gatgatttca aagtgagtct agaatctata   11220
ggtagtttga cacaagaatt agaatataga ggtgaaagtc tattatgcag tttaatattt   11280
agaaatgtat ggttatataa tcaaattgct ctacaattaa aaaatcatgc gttatgtaac   11340
```

-continued

```
aataaattat atttggacat attaaaggtt ctgaaacact taaaaacctt ttttaatctt  11400
gataatattg atacagcatt aacattgtat atgaatttac ccatgttatt tggtggtggt  11460
gatcccaact tgttatatcg aagtttctat agaagaactc ctgatttcct cacagaggct  11520
atagttcact ctgtgttcat acttagttat tatacaaacc atgacttaaa agataaactt  11580
caagatttgt cagatgatag attgaataag ttcttaacat gcataatcac gtttgacaaa  11640
aaccctaatg ctgaattcgt aacattgatg agagatcctc aagctttagg gtctgagaga  11700
caagctaaaa ttactagtga aatcaataga ctggcagtta cagaggtttt gagtacagct  11760
ccaaacaaaa tattctccaa aagtgcacaa cattatacca ctacagagat agatctaaat  11820
gatattatgc aaaatataga acctacatat cctcacgggc taagagttgt ttatgaaagt  11880
ttaccctttt ataaagcaga gaaaatagta aatcttatat caggtacaaa atctataact  11940
aacatactgg aaaagacttc tgccatagac ttaacagata ttgatagagc cactgagatg  12000
atgaggaaaa acataacttt gcttataagg atacttccat tggattgtaa cagagataaa  12060
agagaaatat tgagtatgga aaacctaagt attactgaat taagcaaata tgttagggaa  12120
agatcttggt ctttatccaa tatagttggt gttacatcac ccagtatcat gtatacaatg  12180
gacatcaaat atacaacaag cactatagct agtggcataa ttatagagaa atataatgtt  12240
aacagtttaa cacgtggtga gagaggacca actaaaccat gggttggttc atctacacaa  12300
gagaaaaaaa caatgccagt ttataataga caagtttttaa ccaaaaaaca aagagatcaa  12360
atagatctat tagcaaaatt ggattgggtg tatgcatcta tagataacaa ggatgaattc  12420
atggaagaac tcagcatagg aacccttggg ttaacatatg aaaaggccaa aaaattattt  12480
ccacaatatt taagtgtcaa ctatttgcat cgccttacag tcagtagtag accatgtgaa  12540
ttccctgcat caataccagc ttatagaaca acaaattatc actttgacac tagccctatt  12600
aatcgcatat taacagaaaa gtatggtgat gaagatattg acatagtatt ccaaaactgt  12660
ataagctttg gccttagctt aatgtcagta gtagaacaat ttactaatgt atgtcctaac  12720
agaattattc tcataccktaa gcttaatgag atacatttga tgaaacctcc catattcaca  12780
ggtgatgttg atattcacaa gttaaaacaa gtgatacaaa aacagcatat gttttttacca  12840
gacaaaataa gtttgactca atatgtggaa ttattcttaa gtaacaaaac actcaaatct  12900
ggatctcatg ttaattctaa tttaatattg gcacataaaa tatctgacta ttttcataat  12960
acttacattt taagtactaa tttagctgga cattggattc taattataca acttatgaaa  13020
gattctaaag gtattttga aaaagattgg ggagagggat atataactga tcatatgttt  13080
attaatttga aagttttctt caatgcttat aagacctatc tcttgtgttt tcataaaggt  13140
tatggcaaag caaaactgga gtgtgatatg aacacttcag atcttctatg tgtattggaa  13200
ttaatagaca gtagttattg gaagtctatg tctaaggtat ttttagaaca aaaagttatc  13260
aaatacattc ttagccaaga tgcaagttta catagagtaa aaggatgtca tagcttcaaa  13320
ttatggtttc ttaaacgtct taatgtagca gaatttacag tttgcccttg ggttgttaac  13380
atagattatc atccaacaca tatgaaagca atattaactt atatagatct tgttagaatg  13440
ggattgataa atatagatag aatacacatt aaaaataaac acaaattcaa tgatgaattt  13500
tatacttcta atctcttta cattaattat aacttctcag ataatactca tctattaact  13560
aaacatataa ggattgctaa ttcagaatta gaaaataatt acaacaaatt atatcatcct  13620
acaccagaaa ccctagagaa tatactagcc aatccgatta aaagtaatga caaaagaca  13680
ctgaacgact attgtatagg taaaaatgtt gactcaataa tgttaccatt gttatctaat  13740
aagaagcttg ttaaatcgtc tgcaatgatt agaaccaatt acagcaaaca agacctgtac  13800
aatctattcc ctacggttgt gatcgataga attatagatc attcaggtaa tacagccaaa  13860
tccaaccaac tttacactac tacttcccat caaatatctt tagtgcacaa tagcacatca  13920
ctttattgca tgcttccttg gcatcatatt aatagattca attttgtatt tagttctaca  13980
ggttgtaaaa ttagtataga gtatatttta aaagacctta aaattaaaga tcctaattgt  14040
atagcattca taggtgaagg agcagggaat ttattattgc gtacagtggt ggaacttcat  14100
cctgacataa gatatattta cagaagtctg aaagattgca atgatcatag tttacctatt  14160
gagttttttaa ggctatacaa tggacatatc aacattgatt atggtgaaaa tttgaccatt  14220
cctgctacag atgcaaccaa caacattcat tggtcttatt tacatataaa gtttgctgaa  14280
cctatcagtc tttttgtatg tgatgccgaa ttgcctgtaa cagtcaactg gagtgaaaatt  14340
ataatagaat ggagcaagca tgtaagaaaa tgcaagtact gttcctcagt taataaaatt  14400
acgttaatag taaaatatca tgctcaagat gatattgatt tcaaattaga caatataact  14460
atattaaaaa cttatgtatg cttaggcagt aagttaaagg gatcggaggt ttacttagtc  14520
cttacaatag gtcctgcaaa tatatttcca gtatttaatg tagtacaaaa tgctaaattg  14580
atactatcaa gaaccaaaaa tttcatcatg cctaagaaag ctgataaaga gtctattgat  14640
gcaaatatta aaagtttgat acccttttctt tgttaccctaa taacaaaaaa aggaattaat  14700
actgcattgt caaaactaaa gagtgttgtt agtggagata tactatcata ttctatagct  14760
ggacggaatg aagtttttcag caataaactt ataaatcata gcatatgaa catcttaaag  14820
tggttcaatc atgttttaaa tttcagatca acagaactaa actataacca tttatatatg  14880
gtagaatcta catatccta cctaagtgaa ttgttaaaca gcttgacaac taatgaactt  14940
aaaaaactga ttaaaatcac aggtagtctg ttatacaact ttcataatga ataatgaata  15000
aagatcttat aataaaaatt cctatagcta tacactagca ctgtattcaa ttatagttat  15060
taaaaaatta aaaatcatat aatttttttat aaaaataact tttagtgaac taatcctaaa  15120
gttatcattt tgatcctagga ggaataaatt taaatcccaa tctaattggt ttatatgtgt  15180
attaactaaa ctacgagata ttagtttttg acactttttt tctcgt               15226
```

SEQ ID NO: 119        moltype = DNA   length = 15225
FEATURE                Location/Qualifiers
source                 1..15225
                       mol_type = genomic DNA
                       organism = respiratory syncytial virus
SEQUENCE: 119

```
acgcgaaaaa atgcgtacta caaacttgca cattcggaaa aaatgggggca aataagaatt   60
tgataagtgc tatttaagtc taaccttttc aatcagaaat ggggtgcaat tcactgagca  120
tgataaaggt tagattacaa aatttatttg acaatgacga agtagcattg ttaaaaataa  180
catgttatac tgcacaaatta attcttctga ccaatgcatt agccaaagca gcaatacata  240
caattaaaatt aaacggtata gtttttatac atgttataac aagcagtgaa gtgtgccctg  300
ataacaacat tgtagtaaaa tctaacttta caacaatgcc aatattacaa aacggaggat  360
acatatggga attgattgag ttgacacact gctctcaatt aaacggtcta atggatgata  420
```

```
attgtgaaat caaattttct aaaagactaa gtgactcagt aatgactaat tatatgaatc    480
aaatatctga tttacttggg cttgatctca attcatgaat tatgtttagt ctaactcaat    540
agacatgtgt ttattaccat tttagttaat ataaaaactc atcaaaggga aatggggcaa    600
ataaactcac ctaatcaatc aaactatgag cactacaaat gacaacacta ctatgcaaag    660
attaatgatc acggacatga gaccccctgtc gatggattca ataataacat ctctcaccaa    720
agaaatcatc acacacaaat tcatatactt gataaacaat gaatgtattg taagaaaact    780
tgatgaaaga caagctacat ttacattctt agtcaattat gagatgaagc tactgcacaa    840
agtagggagt accaaataca agaaatacac tgaatatat acaaaatatg gcactttccc    900
catgcctata tttatcaatc atggcgggtt tctagaatgt attggcatta agcctacaaa    960
acacactcct ataatataca aatatgacct caacccgtaa attccaacaa aaaaaaccaa   1020
cccaaccaaa ccaagctatt cctcaaacaa caatgctcaa tagttaagaa ggagctaatc   1080
cgttttagta attaaaaata aaagtaaagc caataacata aattgggca aatacaaaga    1140
tggctcttag caaagtcaag ttaaatgata cattaaataa ggatcagctg ctgtcatcca   1200
gcaaatacac tattcaacgt agtacaggag ataatattga cactcccaat tatgatgtgc   1260
aaaaacacct aaacaaacta tgtggtatgc tattaatcac tgaagatgca aatcatanat   1320
tcacaggatt aataggtatg ttatatgcta tgtccaggtt aggaagggaa gacactataa   1380
agatacttaa agatgctgga tatcatgtta aagctaatgg agtagatata acaacatatc   1440
gtcaagatat aaatggaaag gaaatgaaat tcgaagtatt aacattatca agcttgacat   1500
cagaaataca agtcaatatt gagatagaat ctagaaaatc ctacaaaaaa atgctaaaag   1560
agatgggaga agtggctcca gaatataggc atgattctcc agactgtggg atgataaatac  1620
tgtgtatagc agcacttgta ataaccaaat tagcagcagg agacagatca ggtcttacag   1680
cagtaattag gagggcaaac aatgtcttaa aaaatgaaat aaaacgctac aagggtctca   1740
taccaaagga tatagctaac agtttttatg aagtgtttga aaaacaccct catcttatag   1800
atgtttttgt gcactttggc attgcacaat catcaacaag agggggtagt agagttgaag   1860
gaatctttgc aggattgttt atgaatgcct atggttcagg gcaagtaatg ctaagatggg   1920
gagttttagc caaatctgta aaaaaatatca tgctaggtca tgctagtgtc caggcagaaa   1980
tggagcaagt tgtggaagtc tatgagtatg cacagaagtt gggaggagaa gctggattct   2040
accatatatt gaacaatcca aaagcatcat tgctgtcatt aactcaattt cctaacttct   2100
caagtgtggt cctaggcaat gcagcaggtc taggcataat gggagagtat agaggtacgc   2160
caagaaacca ggatctttat gatgcagcca aagcatatgc agagcaactc aaagaaaatg   2220
gagtaataaa ctacagtgta ttagacttaa cagcagagaa attggaagcc ataaagaatc   2280
aactcaaccc taaagaagat gatgtagagc tttaagttaa caaaaaatac ggggcaaata   2340
agtcaacatg gagaagtttg cacctgaatt tcatggagaa gatgcaaata acaaagctac   2400
caaattccta gaatcaataa agggcaagtt cgcatcatcc aaagatccta agaagaaaga   2460
tagcataata tctgttaact caatagatat agaagtaacc aaagagagcc cgataacatc   2520
tggcaccaac atcatcaatc caacaagtga agccgacagt accccagaaa ccaaagccaa   2580
ctacccaaga aaacccctag taagcttcaa agaagatctc accccaagtg acaacccttt   2640
ttctaagttg tacaaagaaa caatagaaac atttgataac aatgaagaag aatctagcta   2700
ctcatatgaa gagataaatg atcaaacaaa tgacaacatt acagcaagac tagatagaat   2760
tgatgaaaaa ttaagtgaaa tattaggaat gctccataca ttagtagttg caagtgcagg   2820
acccacttca gctcgcgatg gaataagaga tgctatggtt ggtctgagag aagaaatgat   2880
agaaaaaata gagcggaag cattaatgac caatgatagg ttagaggcta tggcaagact   2940
taggaatgag gaaagcgaaa aaatggcaaa agacacctca gatgaagtgc ctcttaatcc   3000
aacttccaaa aaattgagtg acttgttgga agacaacgat agtgacaatg atctgtcact   3060
tgatgatttt tgatcagtga tcaactcact cagcaatcaa caacatcaat aaaacagaca   3120
tcaatccatt gaatcaactg ccagaccgaa caaacaaatg tccgtcagcg gaaccaccaa   3180
ccaatcaatc aaccaactga tccatcagca acctgacgaa attaacaata tagtaacaaa   3240
aaaagaacaa gatggggcaa atatggaaac atacgtgaac aagcttcacg aaggctccac   3300
atacacagca gctgttcagt acaatgttct agaaaaagat gatgatcctg catcactaac   3360
aatatgggtc cctatgttcc agtcatctgt accagcagac ttgctcataa aagaacttgc   3420
aagcatcaac atactagtga agcagatctc tacgcccaaa ggaccttcac tacgagtcac   3480
gattaactca agaagtgctg tgctggctca aatgcctagt aatttcatca taagcgcaaa   3540
tgtatcatta gatgaaagaa gcaaattagc atatgatgta actacacctt gtgaaatcaa   3600
agcatgcagt ctaacatgct taaaagtgaa aagtatgtta actacagtca aagatctac   3660
catgaagaca ttcaacccca ctcatgagat cattgctcta tgtgaatttg aaaatattat   3720
gacatcaaaa agagtaataa taccaaccta tctaagacca attagtgtca aaaacaagga   3780
tctgaactca ctagaaaaca tagcaaccac cgaattcaaa aatgctatca ccaatgcgaa   3840
aattattccc tatgctggat tagtattagt tatcacagtt actgacaata aaggagcatt   3900
caaatatatc aagccacaga gtcaatttat agtagatctt ggtgcctacc tagaaaaaga   3960
gagcatatat tatgtgacta ctaattggaa gcatacagct cacgttttt caatcaaacc   4020
actagaggat taaatttaat tatcaacact gaatgacagg tccacatata tcctcaaact   4080
acacactata tccaaacatc atgaacatct acactacaca cttcatcaca caaccaatc   4140
ccactcaaaa tccaaaatca ctaccagcca ctatctgcta gacctagagt gcgaataggt   4200
aaataaaacc aaaatatggg gtaaatagac attagttaga gttcaatcaa tctcaacaac   4260
catttatacc gccaattcaa tacatatact ataaatctta aaatgggaaa tacatccatc   4320
acaatagaat tcacaagcaa attttggccc tatttacac taatacatat gatcttaact   4380
ctaatctctt tactaattat aatcactatt atgattgcaa tactaaataa gctaagtgaa   4440
cataaaacat tctgtaacaa tactcttgaa ctaggacaga tgcatcaaat caacacatag   4500
tgctctacca tcatgctgtg tcaaattata atcctgtata tataaacaaa caaatccaat   4560
cttctcacag agtcatggtg tcgcaaaacc acgccaacta tcatggtagc atagagtagt   4620
tatttaaaaa ttaacataat gatgaattat tagtatggga tcaaaaacaa cattggggca   4680
aatgcaacca tgtccaaaca caagaatcaa cgcactgcca ggactctaga aaagacctgg   4740
gatactctca atcatctaat tgtaatatcc tcttgtttat acagattaaa tttaaaatct   4800
atagcacaaa tagcactatc agttctggca atgataatct caacctctct cataattgca   4860
gccataatat tcatcatctc tgccaatcac aaagttacac taacaacggt cacagttcaa   4920
acaataaaaa accacactga aaaaacatc accacctacc ttactcaagt cccaccagaa   4980
agggttagct catccaaaca acctacaacc acatcaccaa tccacacaaa ttcagccaca   5040
acatcaccca acacaaagtc agaaacacac cacacaacag cacaaaccaa aggcagaacc   5100
accacctcaa cacagaccaa caagccgagc acaaaaccac gcctaaaaaa tccaccaaaa   5160
```

-continued

```
aaaccaaaag atgattacca ttttgaagtg ttcaacttcg ttccctgtag tatatgtggc   5220
aacaatcaac tttgcaaatc catctgtaaa acaataccaa gcaacaaacc aaagaagaaa   5280
ccaaccatca aacccacaaa caaaccaacc accaaaacca caaacaaaag agacccaaaa   5340
acaccagcca aaacgacgaa aaaagaaact accaccaacc caacaaaaaa accaaccctc   5400
acgaccacag aaagagacac cagcacctca caatccactg tgctcgacac aaccacatta   5460
gaacacacaa tccaacagca atccctccac tcaaccaccc ccgaaaacac acccaactcc   5520
acacaaacac ccacagcatc cgagccctct acatcaaatt ccacccaaaa tacccaatca   5580
catgcttagt tattcaaaaa ctacatctta gcagaaaacc gtgacctatc aagcaagaac   5640
gaaattaaac ctggggcaaa taaccatgga gctgctgatc cacaggttaa gtgcaatctt   5700
cctaactctt gctattaatg cattgtacct cacctcaagt cagaacataa ctgaggagtt   5760
ttaccaatcg acatgtagtg cagttagcag aggttatttt agtgctttaa gaacaggttg   5820
gtataccagt gtcataacaa tagaattaag taatataaaa gaaaccaaat gcaatggaac   5880
tgacactaaa gtaaaactta taaaacaaga attagataag tataagaatg cagtgacaga   5940
attacagcta cttatgcaaa acacaccagc tgccaacaac cgggccagaa gagaagcacc   6000
acagtatatg aactatacaa tcaataccac taaaaaccta aatgtatcaa taagcaagaa   6060
gaggaaacga agatttctgg gcttcttgtt aggtgtagga tctgcaatag caagtggtat   6120
agctgtatcc aaagttctac accttgaagg agaagtgaac aagatcaaaa atgctttgtt   6180
atctacaaac aaagctgtag tcagtctatc aaatgggggc agtgttttaa ccagcaaagt   6240
gttagatctc aagaattaca taaataacca attattaccc atagtaaatc aacagagctg   6300
tcgcatctcc aacattgaaa cagttataga attccagcag aagaacagca gattgttgga   6360
aatcaacaga gaattcagtg tcaatgcagg tgtaacaaca cctttaagca cttacatgtt   6420
aacaaacagt gagttactat cattgatcaa tgatatgcct ataacaaatg atcagaaaaa   6480
attaatgtca agcaatgttc agatagtaag gcaacaaagt tattctatca tgtctataat   6540
aaaggaagaa gtccttgcat atgttgtaca gctacctatc tatggtgtaa tagatacacc   6600
ttgctggaaa ttacacacat cacctctatg caccaccaac atcaaagaag atcaaatat   6660
ttgtttaaca aggactgata gaggatggta ttgtgataat gccaggatcag tatccttctt   6720
tccacaggct gacacttgta aagtacagtc caatcgagta ttttgtgaca ctatgaacag   6780
tttgacatta ccaagtgaag tcagcctttg taacactgac atattcaatt ccaagtatga   6840
ctgcaaaatt atgacatcaa aaacagacat aagcagctca gtaattactt ctcttggagc   6900
tatagtgtca tgctatggta aaactaaatg cactgcatcc aacaaaaatc gtgggattat   6960
aaagacattt tctaatggtt gtgactatgt gtcaaacaaa ggagtagata ctgtgtcagt   7020
gggcaacact ttatactatg taaacaagct ggaaggcaag aacctttatg taaaagggga   7080
acctataata aattactatg accctctagt gtttccttct gatgagtttg atgcatcaat   7140
atctcaagtc aatgaaaaaa tcaatcaaag tttagctttt attcgtagat ctgatgaatt   7200
actacataat gtaaatactg gcaaatctac tacaaatatt atgataacta caattattat   7260
agtaatcatt gtagtattgt tatcattaat agctattggt ttgctgttgt attgcaaagc   7320
caaaaacaca ccagttacac taagcaaaga ccaactaagt ggaatcaata tattgcatt   7380
cagcaaatag acaaaaaacc acctgatcat gtttcaacaa cagtctgctg atcaccaatc   7440
ccaaatcaac ccataacaaa cacttcaaca tcacagtaca ggctgaatca tttcttcaca   7500
tcatgctacc cacacaacta agctagatcc ttaactcata gttacataaa aacctcaagt   7560
atcacaatca aacactaaat caacacatca ttcacaaaat taacagctgg ggcaaatatg   7620
tcgcgaagaa atccttgtaa atttgagatt agaggtcatt gcttgaatgg tagaagatgt   7680
cactacagtc ataattactt tgaatggcct cctcatgcct tactagtgca gcaaacttc   7740
atgttaaaca agatactcaa gtcaatggac aaaagcatag acactttgtc tgaaataagt   7800
ggagctgctg aactggacag aacagaagaa tatgctcttg gtatagttgg agtgctagag   7860
agttacatag gatctataaa caacataaca aaacaatcag catgtgttgc tatgagtaaa   7920
cttcttattg agatcaatag tgatgatatc aaaaagctga gagataatga gaacccaat   7980
tcacctaaga taagagtgta caatactgtt atatcataca ttgagagcaa tagaaaaac   8040
aacaagcaaa caatccatct gctcaaaaga ctaccagcag acgtgctgaa gaagacaata   8100
aaaaacacat tagatatcca caaaagcata atcataagca acccaaaaga gtcaaccgtg   8160
aatgatcaaa atgaccaaac caaaaataat gatattaccg gataaatatc cttgtagtat   8220
atcatccata ttgatttcaa gtgaaagcat gattgctaca ttcaatcata aaaacatatt   8280
acaatttaac cataaccatt tggataacca ccagcgttta ttaaataata tatttgatga   8340
aattcattgg acacctaaaa acttattaga tgccactcaa caatttctcc aacatcttaa   8400
catccctgaa gatatatata caatatatat attagtgtca taatgcttgg ccataacgat   8460
tctatatcat ccaaccataa aactatctta ataaggttat gggacaaaat ggatcccatt   8520
attaatggaa actctgctaa tgtgtatcta actgatagtt atttaaaagg tgttatctct   8580
ttttcagaat gtaatgcttt agggagttac cttttttaacg gcccttatct caaaaatgat   8640
tacaccaact taattagtag acaaagtcca ctactagagc atatgaatct taaaaaacta   8700
actataacac agtcattaat atctagatat cataaaggtg aactgaaatt agaagaacca   8760
acttatttcc agtcattact tatgacatat aaaagcatgt cctcgtctga acaaattgct   8820
acaactaact tacttaaaaa aataatacga gagctatag aaataagtga tgtaaaggtg   8880
tacgccatct tgaataaact aggactaaag gaaaaggaca gagttaagcc caacaataat   8940
tcaggtgatg aaaactcagt acttacaact ataattaaag atgatatact ttcggctggt   9000
gaaagcaatc aatcatatac aaaattcgac aaaaatcact cagtaaatca aaatatcact   9060
atcaaaacaa cactcttgaa aaaattgatg tgttcaatgc aacatcctcc atcatggtta   9120
atacactggt tcaatttata tacaaaatta aataacatat taacacaata tcgatcaaat   9180
gaggtaaaaa gtcatgggtt tatattaata gataatcaaa ctttaagtgg ttttcagtt   9240
attttaaatc aatatggttg tatcgtttat cataaaggac tcaaaaaaat cacaactact   9300
acttacaatc aattttttaac atggaaagac atcagcctta gcagattaaa tgtttgctta   9360
attacttgga taagtaattg tttgaataca ttaaataaaa gcttagggct gagatgtgga   9420
ttcaataatg ttgtgttatc acaattattt ctttatggag attgtatact gaaattattt   9480
cataatgaag gcttctacat aataaaagaa gtagaggga ttattatgtc tttaattcta   9540
aacataacag aagaagatca attaggaaa cgatttttat atggacatgct aaataacatc   9600
acagatgcag ctattaaggc tcaaaagaac ctactatcaa gggtatgtca cactttatta   9660
gacaagacag tgtctgataa tatcataaat ggtaaatgga taatcctatt aagtaaattt   9720
cttaaattga ttaagcttgc aggtgataat aatctcaata atttgagtga gctatatttt   9780
ctcttcagaa tctttggaca tccaatggtt gatgaaagac aagcaatgga tgctgtaaga   9840
attaactgta atgaaactaa gttctactta ttaagtagtc taagtacgtt aagaggtgct   9900
```

-continued

```
ttcatttata gaatcataaa agggtttgta aatacctaca acagatggcc cactttaagg   9960
aatgctattg tcctacctct aagatggtta aactattata aacttaatac ttatccatct  10020
ctacttgaaa tcacagaaaa tgatttgatt attttatcag gattgcggtt ctatcgtgaa  10080
tttcatctgc ctaaaaaagt ggatcttgaa atgataataa atgacaaagc catttcacct  10140
ccaaaagatc taatatggac tagtttttcct agaaattaca tgccatcaca tatacaaat   10200
tatatagaac atgaaaagtt gaagttctct gaaagcgaca gatcaagaag agtactagag  10260
tattacttga gagataataa attcaatgaa tgcgatctat acaattgtgt agtcaatcaa  10320
agctatctca acaactctaa tcacgtggta tcactaactg gtaaagaaag agagctcagt  10380
gtaggtagaa tgtttgctat gcaaccaggt atgtttaggc aaatccaaat cttagcagag  10440
aaaatgatag ccgaaaatat tttacaattc ttccctgaga gtttgacaag atatggtgat  10500
ctagagcttc aaaagatatt agaattaaaa gcaggaataa gcaacaagtc aaatcgttat  10560
aatgataact acaacaatta tatcagtaaa tgttctatca ttacagatct tagcaaattc  10620
aatcaagcat ttagatatga aacatcatgt atctgcagtg atgtattaga tgaactgcat  10680
ggagtacaat ctctgttctc ttggttgcat ttaacaatac ctcttgtcac aataatatgt  10740
acatatagac atgcacctcc tttcataaag gatcatgttg ttaatcttaa tgaagttgat  10800
gaacaaagtg gattatacag atatcatatg ggtggtattg agggctggtg tcaaaaactg  10860
tggaccattg aagctatatc attattagat ctaatatctc tcaaagggaa attctctatc  10920
acagctctga taaatggtga taatcagtca attgatataa gtaaaccagt tagacttata  10980
gagggtcaga cccatgctca agcagattat ttgttagcat taaatagcct taaattgcta  11040
tataaagagt atgcaggtat aggccataag cttaagggaa cagagaccta tatatcccga  11100
gatatgcagt tcatgagcaa aacaatccag cacaatggag tgtactatcc agccagtatc  11160
aaaaaagtcc tgagagtagg tccatggata aatacaatac ttgatgattt taaagttagt  11220
ttagaatcta taggtagctt aacacaggag ttagaataca gagggggaaag cttattatgc  11280
agtttaatat ttaggaacat ttggttatac aatcaaattg ctttgcaact ccgaaatcat  11340
gcattatgta acaataagct atatttagat atattgaaag tattaaaaca cttaaaaact  11400
ttttttaatc ttgatagtat cgatatggcg ttatcattgt atatgaattt gcctatgctg  11460
tttggtggtg gtgatcctaa tttgttatat cgaagctttt ataggagaac tccagacttc  11520
cttacagaag ctatagtaca ttcagtgttt gtgttgagct attatactgg tcacgattta  11580
caagataagc tccaggatct tccagatgat agactgaaca aattcttgac atgtgtcatc  11640
acattcgata aaaatcccaa tgccgagttt gtaacattga tgagggatcc acaggcgtta  11700
gggtctgaaa ggcaagctaa aattactagt gagattaata gattagcagt aacagaagtc  11760
ttaagtatag ctccaaacaa aatattttct aaaagtgcac aacattatac taccactgag  11820
attgatctaa atgacattat gcaaaatata gaaccaactt accctcatgg attaagagtt  11880
gtttatgaaa gtctaccttt ttataaagca gaaaaaaatag ttaatcttat atcaggaaca  11940
aaatccataa ctaatatact tgaaaaaaca tcagcaatag atacaactga tattaatagg  12000
gctactgata tgatgaggaa aaatataact ttacttataa ggatacttcc actagattgt  12060
aacaaagaca aaagagagtt attaagttta gaaaatctta gtataactga attaagcaag  12120
tatgtaagag aaagatcttg gtcattatcc aatatagtag gagtaacatc gccaagtatt  12180
atgttcacaa tggacattaa atatacaact agcactatg ccagtggtat aattatagaa  12240
aaatataatg ttaatagttt aactcgtggt gaaagaggac ctactaagcc atgggtaggt  12300
tcatctacgc aggagaaaaa aacaatgcca gtgtacaata gacaagtttt aaccaaaaag  12360
caaagagacc aaatagattt attagcaaaa ttagactggg tatatgcatc catagacaac  12420
aaagatgaat tcatggaaga actgtgtact ggaacacttg gactgtcata tgaaaaagcc  12480
aaaaagttgt ttccacaata tctaagtgtc aattatttac accgtttaac agtcagtagt  12540
agaccatgtg aattccctgc atcaatacca gcttatagaa caacaaatta tcatttcgat  12600
actagtccta tcaatcatgt attaacagaa aagtatggag atgaagatat cgacattgtg  12660
tttcaaaatt gcataagttt tggtcttagc ctgatgtcgg ttgtggaaca attcacaaac  12720
atatgtccta atagaattat tctcataccg aagctgaatg agatacattt gatgaaacct  12780
cctatattta caggagatgt tgatatcatc aagttgaagc aagtgatacga aaaacagcat  12840
atgttcctac cagataaaat aagtttaacc caatatgtag aattattcct aagtaacaaa  12900
gcacttaaat ctggatctaa catcaattct aatttaatat tagtacataa aatgtctgat  12960
tattttcata atgcttatat tttaagtact aatttagctg gacattggat tctaattatt  13020
caacttatga aagattcaaa aggtattttt gaaaaagatt ggggagaggg gtacataact  13080
gatcatatgt tcattaattt gaatgttttc tttaatgctt ataagactta tttgctatgt  13140
tttcataaag gttatggtaa agcaaaatta gaatgtgata tgaacacttc agatcttctt  13200
tgtgtttttgg agttaataga cagtagctac tggaaatcta tgtctaaagt tttcctagaa  13260
caaaaagtca taaaatacat agtcaatcaa gacacaagtt tgcatagaat aaaaggctgt  13320
cacagtttta gttgtggtt tttaaaacgc cttaataatg ctaaatttac cgtatgccct  13380
tgggttgtta catagatta tcacccaaca catatgaaag ctatattatc ttacatagat  13440
ttagttagaa tggggttaat aaatgtagat aaattaacca ttaaaaataa aaacaaattc  13500
aatgatgaat tttacacatc aaatctcttt tacattagtt ataacttttc agacaacact  13560
catttgctaa caaacaaat aagaattgct aattcagaat tagaagataa ttataacaaa  13620
ctatatcacc caaccccaga aactttagaa aatatatcat taattcctgt taaaagtaat  13680
aatagtaaca aacctaaatt ttgtataagt ggaaataccg aatctataat gatgtcaaca  13740
ttctctaata aaatgcatat taaatcttcc actgttacca caagattcaa ttatagcaaa  13800
caagacttgt acaatttatt tccaaatgtt gtgatagaca ggattataga tcattcaggt  13860
aatacagcaa aatctaacca actttacatc accacttcac atcagacatc tttagtaagg  13920
aatagtgcat cactttattg catgcttcct tggcatcatg tcaataqatt taactttgta  13980
tttagttcca caggatgcaa gatcagtata gagtatattt taaaagatct taagattaag  14040
gaccccagtt gtatagcatt cataggtgaa ggagctggta acttattatt acgtacggta  14100
gtagaacttc atccagacat aagatacatt tacagaagtt taaaagattg caatgatcat  14160
agtttaccta ttgaatttct aagattatac aacgggcata taaacataga ttatggtgag  14220
aatttaacca ttcctgctac agatgcaact aataacattc attggtctta tttacatata  14280
aaatttgcag aacctattag catctttgtc tgcgatgctg aattacctgt tacagccaat  14340
tggagtaaaa ttataattga atggagtaag catgtaagaa agtgcaagta ctgttcttct  14400
gtaaatagat gcattttaat cgcaaaatat catgctcaag atgatattga tttcaaatta  14460
gataacatta ctatattaaa aacttacgtg tgcctaggta gcaagttaaa aggatctgaa  14520
gtttacttag tccttacaat aggccctgca aatatacttc ctgttttttga tgttgtgcaa  14580
aatgctaaat tgattttttc aagaactaaa aatttcatta tgcctaaaaa aactgacaag  14640
```

-continued

```
gaatctatcg atgcaaatat taaaagctta ataccttcc tttgttaccc tataacaaaa  14700
aaaggaatta agacttcatt gtcaaaattg aagagtgtag ttaatgggga tatattatca  14760
tattctatag ctggacgtaa tgaagtattc agcaacaagc ttataaacca caagcatatg  14820
aatatcctaa aatggctaga tcatgtttta aattttagat cagctgaact taattacaat  14880
catttataca tgatagagtc cacatatcct tacttaagtg aattgttaaa tagtttaaca  14940
accaatgagc tcaagaaact gattaaaata acaggtagtg tactatacaa ccttcccaac  15000
gaacagtaac ttaaaatatc attaacaagt ttggtcaaat ttagatgcta acacatcatt  15060
atattatagt tattaaaaaa tatgcaaact tttcaataat ttagcttact gattccaaaa  15120
ttatcatttt atttttaagg ggttgaataa aagtctaaaa ctaacaatga tacatgtgca  15180
tttacaacac aacgagacat tagtttttga cactttttt ctcgt             15225
```

COMPOSITIONS AND METHODS FOR DETECTION OF VIRAL PATHOGENS IN SAMPLES

CROSS REFERENCE TO RELATED APPLICATIONS

This application is a divisional of U.S. Provisional application Ser. No. 16/488,909, filed Aug. 26, 2019, which is a national stage entry of PCT/US2018/023995, filed Mar. 23, 2018, which claims priority under 35 U.S.C. § 119 of U.S. Provisional Application 62/476,659, filed Mar. 24, 2017, the contents of each of which are incorporated herein by reference.

SEQUENCE LISTING

The Sequence Listing written in file DIA.0049_SeqList-ST26.xml is 65 kilobytes in size, was created Apr. 2, 2024, and is hereby incorporated by reference.

BACKGROUND

Field

The present disclosure relates to the field of biotechnology. More specifically, the disclosure relates to compositions, including kits and reagents, and methods for analysis of samples to detect viral pathogens, particularly Influenza Virus and Respiratory Syncytial Virus.

Background

Influenza is an acute respiratory illness in humans caused by infection with the Influenza (Flu) virus, primarily types A and B. Influenza A viruses are further categorized into subtypes based on two major surface protein antigens, hemagglutinin (H), and neuraminidase (N). Influenza B viruses are not categorized into subtypes. The Influenza viruses are RNA viruses in the family Orthomyxoviridae. Each of Influenza types A and B (Flu A and Flu B, respectively) is a separate genus containing one species and a large number of sub-species.

Influenza epidemics occur yearly around the world. Although both Flu types A and B circulate in the population, type A is usually dominant. These yearly epidemics are partly due to antigenic variation in the H and N surface proteins of the virus. Transmission of influenza is primarily via airborne droplet (coughing or sneezing). Symptoms arise on average 1 to 2 days post-exposure and include fever, chills, headache, malaise, cough, and coryza. Gastrointestinal symptoms such as nausea, vomiting, and diarrhea can occur, primarily in young children. Complications due to influenza include pneumonia, which can cause increased morbidity and mortality in pediatric, elderly, and immune-compromised populations. In the United States, it is estimated that influenza results in more than 200,000 hospitalizations and up to 36,000 deaths annually. Large influenza outbreaks, or pandemics, occur rarely. In the 20$^{th}$ Century, three influenza pandemics occurred, in 1918, 1958, and 1968, each causing millions of deaths worldwide. Influenza may also affect other animals, including pigs, horses and birds.

Respiratory syncytial virus (RSV) is the leading cause of lower respiratory tract infections in infants and children. Like Influenza, RSV is an RNA virus. RSV is a member of the family Paramyxoviridae, in the genus Orthopneumovirus. There are 2 types of RSV, A and B, which are differentiated based on antigenic and surface protein variations. Most yearly epidemics contain a mix of RSV A and RSV B, but one subgroup can dominate during a season. RSV infection can cause severe respiratory illness among all ages but is more prevalent in pediatric, elderly, and immune-compromised populations. RSV can infect up to 80% of children less than 1 years of age. Bronchiolitis and pneumonia are the major clinical complications in infants and young children, resulting in an estimated 51,000-82,000 hospital admissions per year in the United States. RSV infection is also an important cause of severe respiratory disease and substantial number of deaths in the elderly, with an estimated annual cost of $150 to $680 million for RSV pneumonia hospitalizations.

Given the morbidity, mortality, and economic costs associated with Influenza and RSV infections, there clearly exists a need for improved detection of these pathogens. This disclosure addresses this and other needs.

BRIEF DESCRIPTION

This disclosure provides compositions, including kits and reagents, and methods for in vitro diagnostic analysis of Influenza A Virus (Flu A), Influenza B Virus (Flu B), Respiratory Syncytial Virus type A (RSV A) or Respiratory Syncytial Virus type B (RSV B) nucleic acids in a sample. Preferably the in vitro diagnostic analysis utilizes polymerase chain reactions (PCR), though other in vitro assay methodologies are contemplated for use with the disclosed compositions. A particularly useful in vitro assay for use with the Flu A, Flu B, RSV A or RSV B target nucleic acids is a reverse transcription PCR assay, as these target nucleic acids are RNA viruses. Conveniently, in vitro amplification assays can performed simultaneously with in vitro detection assays (real-time PCR). Thus, a particularly useful and convenient in vitro assay for use with the Flu A, Flu B, RSV A or RSV B target nucleic acids is a real-time, reverse transcription PCR assay.

It should be noted that, as used in this specification and the appended claims, the singular form "a," "an," and "the" include plural references unless the context clearly dictates otherwise. Thus, for example, reference to "an oligonucleotide" includes a plurality of oligonucleotides and the like. The conjunction "or" is to be interpreted in the inclusive sense, i.e., as equivalent to "and/or," unless the inclusive sense would be unreasonable in the context.

It will be appreciated that there is an implied "about" prior to the temperatures, concentrations, times, etc. discussed in the present disclosure, such that slight and insubstantial deviations are within the scope of the present teachings herein. In general, the term "about" indicates insubstantial variation in a quantity of a component of a composition not having any significant effect on the activity or stability of the composition. All ranges are to be interpreted as encompassing the endpoints in the absence of express exclusions such as "not including the endpoints"; thus, for example, "within 10-15" includes the values 10 and 15 and all whole and partial (when applicable) values there between.

Unless specifically noted, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims). "Consisting essentially of" means that additional component(s), composition(s) or method step(s) that do not materially change the basic and novel characteristics of the compositions and methods described herein may be included in those compositions or methods. Such characteristics include the ability to detect a target nucleic acid present in a sample with specificity that distinguishes the target nucleic acid from other known respiratory pathogens. Any component(s), composition(s), or method step(s) that have a material effect on the basic and novel characteristics of the present disclosure would fall outside of this term.

The term "complement" refers to a nucleic acid molecule that comprises a contiguous nucleotide sequence that is complementary to a contiguous nucleic acid sequence of another nucleic acid molecule (for standard nucleotides A:T, A:U, C:G). For example 5'-AACTGUC-3' is the complement of 5'-TTGACAG-3'. Two nucleic acid sequences are "sufficiently complementary" when, their respective contiguous nucleic acid sequences are at least 70% complementary. (see, e.g., See Sambrook, et al., Molecular Cloning, A Laboratory Manual, $2^{nd}$ ed. (Cold Spring Harbor Laboratory Press, Cold Spring Harbor, N.Y., 1989)).

"Perfectly matched" in reference to a nucleic acid duplex means that the poly- or oligonucleotide strands making up the duplex form a double-stranded structure, or region of double-stranded structure, with one another such that every nucleotide (or nucleotide analogue) in each strand undergoes Watson-Crick base-pairing with a nucleotide in the other strand in the duplexed (i.e., hybridized) region. The term also comprehends the pairing of nucleoside analogues, such as deoxyinosine, nucleosides with 2-aminopurine bases, and the like. Conversely, a "mismatch" in a nucleic acid duplex means that one or more pairs of nucleotides in the duplex fail to undergo Watson-Crick base-pairing.

By "substantially homologous," "substantially corresponding", or "substantially corresponds" is meant a nucleic acid molecule comprises a contiguous nucleic acid sequence that is at least 70% homologous to a contiguous nucleic acid sequence of another nucleic acid molecule.

A "sample" or "biological sample" is any tissue or polynucleotide-containing material obtained from a human, animal, or environmental sample and which may contain a target nucleic acid. Biological samples include peripheral blood, mucus, plasma, serum, saliva, cerebrospinal fluid, urine, or other body fluid, bone marrow, or other organ, biopsy tissue, or other materials of biological origin, as well as solutions or compositions containing materials of biological origin, for example, a bronchial lavage fluid. Samples can be obtained from a number of sources, including a clinical source wherein the sample is collected in order to determine the presence or absence of a target nucleic acid in the sample and in turn provide a patient with a diagnosis. A sample may be chemically and/or mechanically treated to disrupt tissue or cell structure, thereby releasing intracellular components into a solution.

The term "nucleotide" is defined herein to include both nucleotides and nucleosides, including deoxyribonucleotides (e.g., dATP, dCTP, dGTP, dTTP), ribonucleotides (e.g., rATP, rCTP, rGTP, rUTP), and analogues thereof. Nucleotides comprise a purine or pyrimidine base linked glycosidically to a ribose or a deoxyribose sugar and a phosphate group attached to the ribose or deoxyribose sugar. Nucleosides comprise a purine or pyrimidine base linked glycosidically to a ribose or a deoxyribose sugar, but lack the phosphate residues that are present in a nucleotide. Nucleotides and nucleosides, as used herein, refer to a monomer of DNA or RNA, respectively. (See e.g., Komberg and Baker, DNA Replication, $2^{nd}$ Ed. (Freeman, San Francisco, 1992)).

The term "analogue", in reference to a chemical compound, refers to compound having a structure similar to that of another one, but differing from it in respect of one or more different atoms, functional groups, or substructures that are removed or replaced with one or more other atoms, functional groups, or substructures. In the context of a nucleotide or nucleoside, an analog refers to a compound that, like the nucleotide/side of which it is an analog, can be incorporated into a nucleic acid molecule (e.g., a primer, a probe and/or an amplification product). Nucleotide/side analogs are commonly added to synthetic oligonucleotides (such as primers and probes) using phosphoramidite chemistry techniques and devices. Nucleotide/side analogs are commonly added to amplification products by including the analog in a reaction mixture wherein a suitable polymerase, for example, a DNA polymerase, will incorporate the analog into the amplification product. Nucleotide/side (hereinafter "nucleotide") analogs include synthetic nucleotides having modified base moieties and/or modified sugar moieties and/ or modified phosphate groups, see, e.g., Scheit, Nucleotide Analogues (John Wiley, New York, 1980); Uhlman and Peyman, Chemical Reviews, 90:543-584 (1990), or the like. Such analogues include synthetic nucleosides designed to enhance binding properties, reduce complexity, increase specificity, and the like.

"DNA" refers to deoxyribonucleic acid, a polymer of deoxyribonucleotides linked by phosphodiester bonds. DNA can be single-stranded (ssDNA) or double-stranded (dsDNA), and can include both single and double-stranded (or "duplex") regions. "RNA" refers to ribonucleic acid, a polymer of ribonucleotides linked by phosphodiester bonds. RNA can be single-stranded (ssRNA) or double-stranded (dsRNA), and can include both single and double-stranded (or "duplex") regions. Single-stranded DNA (or regions thereof) and ssRNA can, if sufficiently complementary, hybridize to form double-stranded complexes (or regions). By "RNA equivalent", "DNA equivalent", "RNA equivalent bases" and "DNA equivalent bases" is meant RNA and DNA molecules having similar complementary base pair hybridization properties. RNA and DNA equivalents have different sugar moieties (i.e., ribose versus deoxyribose) and may differ, for example, by the presence of uracil in RNA and thymine in DNA. The differences between RNA and DNA equivalents do not contribute to differences in homology (or sequence identity) because the equivalents have the same degree of complementarity to a particular sequence.

The terms "polynucleotide" or "oligonucleotide" (used synonymously herein) mean a multimeric compound comprising two or more joined RNA nucleotides, DNA nucleotides, analogs of RNA nucleotides, analogs of DNA nucleotides, or combinations thereof. Polynucleotides can include other molecules that may be present in a joined sequence of nucleotides and that do not prevent hybridization of the polynucleotide with a second molecule having a complementary sequence. For example, a polynucleotide can include two or more joined nucleotides on a first side of a linker molecule and two or more joined nucleotides on a second side of the linker molecule, as is often the configuration of a molecular torch. Polynucleotides are preferably a polymeric chain of from 10 to 200 contiguous nucleotides. Polynucleotides may be purified from naturally occurring sources, but preferably are synthesized using any of a variety of well-known enzymatic or chemical methods. Whenever an oligonucleotide (or other nucleic acid) is represented by a sequence of letters, such as "ATGCUCTG", unless otherwise indicated, it will be understood that the nucleotides are in 5'-3' orientation from left to right and that "A" denotes adenosine (dATP/rATP) or an analogue thereof, "C" denotes cytidine (dCTP/rCTP) or an analogue thereof, "G" denotes guanosine (dGTP/rGTP) or an analogue thereof, "U" denotes uracil (rUTP) or an analogue thereof, and "T" denotes thymidine (dTTP) or an analogue thereof, unless otherwise noted. Usually oligonucleotides of the disclosure comprise the four natural nucleotides; however, they may also comprise non-natural nucleotide analogues.

A "probe" is an oligonucleotide that hybridizes specifically to a target nucleic acid sequence in a nucleic acid, preferably in an amplified nucleic acid, under conditions that promote hybridization, to form a detectable hybrid. Probe oligonucleotides comprise one or more of a contiguous nucleotide sequence, a target hybridizing sequence, a non-target hybridizing sequence, detectable labels, linkers, and nucleotide analogs. Probes preferably have oligonucleotide lengths from about 10 contiguous nucleotides up to 100 contiguous nucleotides. Certain specific probes that are preferred have target-hybridizing sequences in the length range of from 12-87, from 10-20, from 13-37, or from 17-23 nucleotides. A probe sequence may comprise RNA, DNA, analogs, and combinations thereof. The "backbone" of a probe may be made up of a variety of linkages known in the art, including one or more sugar-phosphodiester linkages, peptide-nucleic acid bonds (PNAs), phosphorothioate linkages, methylphosphonate linkages, or combinations thereof. Sugar moieties of the probe may be either ribose or deoxyribose, or similar compounds having known substitutions, such as, for example, 2'-O-methyl ribose and 2' halide substitutions (e.g., 2'-O-Me or 2'-F). The nucleotide analogues incorporated into a probe oligonucleotide sequence can include inosine or "I", 5-Me-dC, isoguanine, other derivatives of purine or pyrimidine bases, or abasic residues (e.g., nucleoside residues (e.g., The Biochemistry of the Nucleic Acids, pages 5-36, Adams, et al., ed., 11$^{th}$ ed., 1992; PCT pub. no. WO 93/13121) The target nucleic acid sequence of a probe generally refers to a sequence contained within an amplified nucleic acid molecule that hybridizes specifically to at least a portion of the probe oligonucleotide using standard hydrogen bonding.

A probe may comprise target-specific sequences and optionally other sequences that are non-target hybridizing sequences (e.g., a sequence that does not hybridize the nucleic acid to be detected. Such non-target hybridizing sequences can include, for example, a promoter sequence, a restriction endonuclease recognition site, or sequences that contribute to three-dimensional conformation of the probe (e.g., see U.S. Pat. Nos. 5,118,801 and 5,312,728). Probes exhibiting at least some degree of self-complementarity include molecular torches and molecular beacons.

"Molecular Torches" can be designed to include distinct regions of self-complementarity (coined "the target hybridizing sequence domain" and "the target closing domain") that are connected by a joining region and which hybridize to one another under predetermined hybridization assay conditions. When exposed to denaturing conditions, the two complementary regions (which may be fully or partially complementary) of a molecular torch melt, leaving the target hybridizing sequence domain available for hybridization to a target nucleic acid sequence when the predetermined hybridization assay conditions are restored. Molecular torches are designed so that the target hybridizing sequence domain favors hybridization to the target nucleic acid sequence over the target closing domain. The target hybridizing sequence domain and the target closing domain of a molecular torch include interacting labels (e.g., fluorescent/quencher) positioned so that a different signal is produced when the molecular torch is self-hybridized as opposed to when the molecular torch is hybridized to a target nucleic acid sequence, thereby permitting detection of probe:target duplexes in a test sample in the presence of unhybridized probe having a viable label associated therewith. Molecular Torches are described, for example, in U.S. Pat. No. 6,361, 945.

A "Molecular Beacon" can be designed to have a target hybridizing sequence, an affinity pair (or nucleic acid arms) holding the probe in a closed conformation in the absence of a target nucleic acid sequence, and a label pair that interacts when the probe is in a "closed" conformation. Hybridization of the target hybridizing sequence of the molecular beacon to its intended target nucleic acid sequence separates the members of the affinity pair, thereby shifting the probe to an "open" conformation. The shift to the "open" conformation is detectable due to reduced interaction of the label pair. Molecular Beacons are described, for example, in U.S. Pat. No. 5,925,517.

A probe optionally may contain a detectable label that either may be attached to the end of the probe or attached internally on the probe. The terms "label" or "detectable label" are used interchangeably herein and refer to one or more atoms that can be specifically detected to indicate the presence of a substance to which the one or more atoms is attached. A label can be a primary label that is directly detectable or secondary label that can be indirectly detected, for example, via direct or indirect interaction with a primary. A label can be linked to polynucleotide probes either directly or indirectly. Labels include dyes, particles, chromophores (e.g., an atom or molecule that imparts a detectable color), combinatorial fluorescence energy transfer labels, electrophores, redox active moieties (e.g., transition metals), enzymes, haptens, luminescent compounds (e.g., bioluminescent, phosphorescent, or chemiluminescent moieties), fluorophores, mass labels, and radiolabels. Labels and related detections methods are well known (see e.g., U.S. Pat. No. 6,627,748 (B1); Styer and Haugland, (1967), Proc. Natl. Acad. Sci. U.S.A. 98:719; U.S. Pat. Nos. 5,591,578; 5,491,063; 5,201,015)

The term "fluorophore" means a fluorescent chemical compound that can re-emit light upon light excitation. Fluorophores include, for example, fluorescent lanthanide complexes, including those of Europium and Terbium, fluorescein, rhodamine, tetramethylrhodamine, eosin, erythrosin, coumarin, methyl-coumarins, pyrene, Malacite green, Cy3, Cy5, CalFluor Red™, CalFluor Orange™, stilbene, Quasar dyes (e.g., Quasar 570, Quasar 670, Quasar 705), Lucifer Yellow, Cascade Blue™, Texas Red, Alexa dyes, phycoerythrin, Bodipy, and others known in the art, see, e.g., Haugland, Molecular Probes Handbook (Eugene, OR), 6th Edition; The Synthegen catalog (Houston, Tex.); Lakowicz, Principles of Fluorescence Spectroscopy, 2nd Ed., Plenum Press New York (1999), and WO 98/59066.

The term "quencher" is used to refer to a molecule that absorbs light. Quenchers are commonly used in combination with a light emitting label such as a fluorophore to absorb emitted light when in close proximity to the fluorophore. Quenchers are well-known in the art and include, e.g., Black Hole Quencher™ (or BHQ™, BHQ-1™, or BHQ-2™) Blackberry Quencher, Dabcyl, QSY, and Tamra™ compounds, to name a few.

A "homogeneous detectable label" refers to a label that associates with a probe oligonucleotide and that can be detected without physically removing hybridized from unhybridized forms of the label or labeled probe. Examples of homogeneous labels have been described in detail in, for example, U.S. Pat. Nos. 5,283,174; 6,150,097; 5,201,015; 5,656,207; and 5,658,737.

Linear probes, molecular torches and beacons are preferably labeled with an interactive pair of detectable labels. Examples of detectable labels that are preferred as members of an interactive pair of detectable labels interact with each other by FRET or non-FRET energy transfer mechanisms. Fluorescence resonance energy transfer (FRET) involves the radiationless transmission of energy quanta from the site of absorption to the site of its utilization in the molecule, or system of molecules, by resonance interaction between chromophores, over distances considerably greater than interatomic distances, without conversion to thermal energy, and without the donor moiety and acceptor moiety coming into kinetic collision. The "donor" is the moiety that initially absorbs and then transfers the energy, and the "acceptor" is the moiety to which the energy is subsequently transferred. In addition to FRET, there are at least three other "non-FRET" energy transfer processes by which excitation energy can be transferred from a donor to an acceptor molecule.

When the two labels of a donor/acceptor pair are held sufficiently close that energy emitted by one label can be received or absorbed by the second label, whether by a FRET or non-FRET mechanism, the two labels are said to be in "energy transfer relationship" with each other. This is the case, for example, when a molecular beacon or molecular torch is maintained in the "closed" state by formation of a stem duplex, and fluorescent emission from a fluorophore attached to one arm of the probe is quenched by a quencher moiety on the opposite arm. This is also the case when, for example, a linear probe is labeled with a fluorophore and a quencher at a distance along the linear probe that fluorescent emission from the attached fluorophore is quenched by the attached quencher. In these instances, the spatial separation of the fluorophore and quencher molecules (e.g., by "opening" the molecular torch or beacon or by hydrolyzing the linear probe molecule).

Examples of donor/acceptor pairs, include fluorescein/ tetramethylrhodamine, IAEDANS/fluororescein, EDANS/ DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, CalOrange/BHQ1, CalRed/BHQ2, FAM/BHQ1, Quasar/ BHQ2, Texas Red/DABCYL, CY5/BH1, CY5/BH2, CY3/ BH1, CY3/BH2 and fluorescein/QSY7 dye. Labels are available from LGC Biosearch Technologies (Petaluma, CA), Glen Research (Sterling, VA), Integrated DNA Technologies (Skokie, Il); Thermo Fisher (Waltham, MA), and others.

Synthetic techniques and methods of bonding labels to nucleic acids and detecting labels are well known in the art (e.g., see Sambrook, et al., Molecular Cloning, A Laboratory Manual, $2^{nd}$ ed. (Cold Spring Harbor Laboratory Press, Cold Spring Harbor, N.Y., 1989), Chapter 10; U.S. Pat. Nos. 5,658,737, 5,656,207, 5,547,842, 5,283,174, and 4,581,333, and published European Pat. App. No. 0 747 706). A probe may optionally contain a fluorophore and a quencher. The nucleotide residues of the probe that combine with the target nucleic acid sequence need not be strictly contiguous, as may be the case with a detectable moiety internal to the sequence of the probe.

An "amplification primer" or "primer" is an optionally modified oligonucleotide that hybridizes to a target nucleic acid sequence, or its complement, and can participate in a nucleic acid amplification reaction. Primer oligonucleotides comprise one or more of a contiguous nucleotide sequence, a target hybridizing sequence, a non-target hybridizing sequence, linkers, and nucleotide analogs. Primers preferably have oligonucleotide lengths from about 10 contiguous nucleotides up to 100 contiguous nucleotides. A primer sequence may comprise RNA, DNA, analogs, and combinations thereof. The "backbone" of a primer may be made up of a variety of linkages known in the art, including one or more sugar-phosphodiester linkages, peptide-nucleic acid bonds (PNAs), phosphorothioate linkages, methylphosphonate linkages, or combinations thereof. Sugar moieties of the primer may be either ribose or deoxyribose, or similar compounds having known substitutions, such as, for example, 2'-O-methyl ribose and 2' halide substitutions (e.g., 2'-O-Me or 2'-F). The nucleotide analogues incorporated into a primer oligonucleotide sequence can include inosine or "I", 5-Me-dC, isoguanine, other derivatives of purine or pyrimidine bases, or abasic residues (e.g., nucleoside residues). The target nucleic acid sequence of a primer generally refers to both a sequence contained within the genetic information of an organism to be detected and a sequence contained within an amplified nucleic acid molecule that hybridizes specifically to at least a portion of the primer oligonucleotide using standard hydrogen bonding. Primers hybridize to a target nucleic acid sequence and have a 3' end that can be extended by a DNA polymerase that incorporates nucleotides complementary to the target nucleic acid sequence to generate a double stranded portion thereof.

By "capture oligonucleotide" is meant at least one nucleic acid oligonucleotide that allows for joining of a target nucleic acid and an immobilized oligonucleotide due to base pair hybridization (preferably resulting in an immobilized probe:capture oligonucleotide:target nucleic acid complex). A capture oligonucleotide preferably includes two binding regions: a target nucleic acid-binding region and an immobilized probe-binding region, usually contiguous on the same oligonucleotide, although the capture oligonucleotide may include a target nucleic acid-binding region and an immobilized probe-binding region that are present on two different oligonucleotides joined together by one or more linkers. For example, an immobilized probe-binding region may be present on a first oligonucleotide, the target nucleic acid-binding region may be present on a second oligonucleotide, and the two different oligonucleotides are joined by hydrogen bonding with a linker that is a third oligonucleotide containing sequences that hybridize specifically to the sequences of the first and second oligonucleotides. The target hybridizing region of a capture probe can be specific for the target nucleic acid (e.g., sufficiently complementary to the target nucleic acid sequence) or non-specific for the target nucleic acid. One target capture system that includes a capture oligonucleotide is described in U.S. Pat. Nos. 6,110,678 & 9,051,601.

By "immobilized probe" or "immobilized nucleic acid" is meant a nucleic acid that joins, directly or indirectly, a capture oligonucleotide to an immobilized support. An immobilized probe is an oligonucleotide joined to a solid support that facilitates separation of bound target nucleic acids from unbound material in a sample.

The term "solid substrate" means any suitable medium present in the solid phase to which an antibody or an agent can be covalently or non-covalently affixed or immobilized.

By "separating" or "purifying" or "isolating" is meant that one or more components of the biological sample are removed from one or more other components of the sample. Sample components include nucleic acids in a generally aqueous solution phase that can also include other materials, for example, proteins, carbohydrates, lipids, and labeled probes. Preferably, the separating, isolating, or purifying step removes at least about 70%, more preferably at least about 90% and, even more preferably, at least about 95% of the other components present in the sample.

A "homogeneous assay" refers to a detection procedure that does not require physical separation of hybridized probe from non-hybridized probe prior to determining the extent of specific probe hybridization. Exemplary homogeneous assays can employ molecular beacons or other self-reporting probes that emit fluorescent signals when hybridized to an appropriate target nucleic acid sequences, chemiluminescent acridinium ester labels that can be selectively destroyed by chemical means unless present in a hybrid duplex, and other homogeneously detectable labels that will be familiar to those having an ordinary level of skill in the art.

"Amplification" refers to an in vitro procedure for obtaining multiple copies of a target nucleic acid sequence, its complement, or fragments thereof.

"Amplicon" refers to a DNA or RNA that is the product of a nucleic acid amplification or replication process. It can be formed using various methods, including polymerase chain reaction (PCR), ligase chain reaction (LCR), a transcription-associated amplification (e.g., TMA) etc.

The term "multiplex PCR" refers as a PCR reaction characterized in that two or more different amplification products, or amplicons, are generated by means of using two or more pairs of amplification primers in the same PCR reaction.

The term "multicolor" RT-PCR refers to a real time PCR assay characterized in that one or more different amplification products, or amplicons, generated either in a multiplex PCR or in a monoplex PCR (using only one pair of amplification primers) are (is) detected by using distinguishably labeled hybridization probes.

By "target nucleic acid" or "target" is meant a nucleic acid containing a target nucleic acid sequence. Described herein, target nucleic acids include Flu A nucleic acids, Flu B nucleic acids, RSV A nucleic acids and RSV B nucleic acids. By "target nucleic acid sequence", (also referred to as "target nucleotide sequence", "target sequence", "target region", "target nucleic acid molecule"), is meant a specific deoxyribonucleotide or ribonucleotide molecule or nucleotide sequence comprising all or part of the nucleotide sequence of a single-stranded nucleic acid molecule, and the deoxyribonucleotide or ribonucleotide sequence complementary thereto.

By "transcription associated amplification" is meant any type of nucleic acid amplification that uses an RNA polymerase to produce multiple RNA transcripts from a nucleic acid template. One example of a transcription associated amplification method, called "Transcription Mediated Amplification" (TMA), generally employs an RNA polymerase, a DNA polymerase, deoxyribonucleoside triphosphates, ribonucleoside triphosphates, and a promoter-template complementary oligonucleotide, and optionally may include one or more analogous oligonucleotides. Variations of TMA are well known in the art and are described, for example, in U.S. Pat. Nos. 5,437,990; 5,399,491; 5,554,516; 5,130,238; 4,868,105; and 5,124,246; published PCT application nos. WO 93/22461, WO 88/01302, WO 88/10315, WO 94/03472, and WO 95/03430.

10

SUMMARY

This disclosure provides compositions, including kits and reagents, and methods for in vitro diagnostic analysis of Influenza A Virus (Flu A), Influenza B Virus (Flu B), Respiratory Syncytial Virus type A (RSV A) or Respiratory Syncytial Virus type B (RSV B) nucleic acids in a sample. Preferably the in vitro diagnostic analysis utilizes polymerase chain reactions (PCR), though other in vitro assay methodologies are contemplated for use with the disclosed compositions. A particularly useful in vitro assay for use with the Flu A, Flu B, RSV A or RSV B target nucleic acids is a reverse transcription PCR assay, as these target nucleic acids are RNA viruses. Conveniently, in vitro amplification assays can performed simultaneously with in vitro detection assays (real-time PCR). Thus, a particularly useful and convenient in vitro assay for use with the Flu A, Flu B, RSV A or RSV B target nucleic acids is a real-time, reverse transcription PCR assay.

In one aspect, the sample is a biological sample. In one aspect the biological sample is a clinical sample. In another aspect the sample is a swab sample, for example, from nasopharyngeal (NP) swab specimens obtained from a patient. In some embodiments, the compositions and methods can be used to aid in the differential diagnosis of Flu A, Flu B, and RSV A and RSV B infections. Negative results do not preclude such infection. Conversely, positive results do not rule-out bacterial infections or co-infections with other viruses. The use of additional laboratory testing and clinical presentation may also be considered in order to obtain the final diagnosis of respiratory viral infection.

One aspect provides nucleic acid molecules that are hybridization assay probes useful for detecting Flu A, Flu B, RSV A, or RSV B target nucleic acid sequences. Preferably, such probe molecule species include a probe sequence that is substantially complementary to a probe target nucleic acid sequence in the viral genome, or an amplicon generated therefrom, being targeted for detection. In preferred embodiments, the probe target nucleic acid sequence consists of about 17 to about 100 contiguous bases contained within targeted viral genome (or amplicon generated therefrom). Preferably, a probe molecule is up to about 100 nucleotide residues in length, although lengths of between about 20-60 nucleotide residues are particularly preferred.

In the context of Flu A, in some preferred embodiments the probe comprises a sequence that is preferably SEQ NAME: FA1-F, SEQ NAME: FA1-G, SEQ NAME: FA1-H, SEQ NAME: FA1-I, SEQ NAME: FA1*-J, SEQ NAME: FA1*-K, SEQ NAME: FA1-L, SEQ NAME: FA1-M, SEQ NAME: FA1-N, SEQ NAME: FA1*-O, SEQ NAME: FA1*-P, or SEQ NAME: FA1*-Q. In other embodiments, the probe sequence is preferably SEQ NAME: FA2-R, SEQ NAME: FA2-S, SEQ NAME: FA2-T, SEQ NAME: FA2*-U, or SEQ NAME: FA2*-V (SEQ ID NOS:6 to 22). In particularly preferred embodiments, two probes, one from each of the foregoing groups, are used in tandem to target two different regions of the Flu A genome or amplification products generated therefrom.

In the context of Flu B, in preferred embodiments the probe sequence is preferably SEQ NAME: FB-B, SEQ NAME: FB-B!, SEQ NAME: FB-C, SEQ NAME: FB-C!, SEQ NAME: FB-D, SEQ NAME: FB-D!, SEQ NAME: FB-E, SEQ NAME: FB-E!, SEQ NAME: FB-F, SEQ NAME: FB-F!, SEQ NAME: FB-G, SEQ NAME: FB-G!, SEQ NAME: FB-H, SEQ NAME: FB-H!, SEQ NAME: FB-I, SEQ NAME: FB-I!, SEQ NAME: FB-J, SEQ NAME: FB-J!, SEQ NAME: FB-K, SEQ NAME: FB-K!, SEQ NAME: FB-L, SEQ NAME: FB-L!, SEQ NAME: FB-M, SEQ NAME: FB-M!, SEQ NAME: FB-N, SEQ NAME: FB-N!, SEQ NAME: FB-O, SEQ NAME: FB-O!, SEQ NAME: FB-Q, SEQ NAME: FB-R, SEQ NAME: FB-S, SEQ NAME: FB-T, SEQ NAME: FB-U, SEQ NAME: FB-V, SEQ NAME: FB*-W, or SEQ NAME: FB*-X (SEQ ID NOS:30 to 57 & 59 to 66).

In the context of RSV A, in preferred embodiments the probe sequence is preferably SEQ NAME: RA-A, SEQ NAME: RA-E, SEQ NAME: RA-F, SEQ NAME: RA-G, SEQ NAME: RA-H, SEQ NAME: RA-J, SEQ NAME: RA-J!, SEQ NAME: RA-K, SEQ NAME: RA-K!, SEQ NAME: RA-L, SEQ NAME: RA-L!, SEQ NAME: RA-M, SEQ NAME: RA-M!, SEQ NAME: RA-O, SEQ NAME: RA-P, SEQ NAME: RA-Q, SEQ NAME: RA*-W, and SEQ NAME: RA*-X (SEQ ID NOS:71, 75 to 78, 80 to 87, 89 to 91, 97 & 98).

In the context of RSV B, in preferred embodiments the probe sequence is preferably SEQ NAME: RB-D, SEQ NAME: RB-E, SEQ NAME: RB-V, SEQ NAME: RB-V!, SEQ NAME: RB-W, SEQ NAME: RB-W!, SEQ NAME: RB-X, SEQ NAME: RB-X!, SEQ NAME: RB-Y, and SEQ NAME: RB-Y! (SEQ ID NOS: 102, 103, & 107 to 114).

Preferably, a probe molecule species is labeled, optionally distinguishably labeled such that any one probe molecule species can be distinguished from other probe molecule species in a multiplex detection assay. Distinguishable labeling can be achieved using two or more detectable labels, for example, a chemiluminescent moiety, a fluorophore moiety, and both a fluorophore moiety and a quencher moiety.

Another aspect the disclosure concerns nucleic acid molecules that are amplification primers engineered for use in in vitro amplification of target nucleic acid sequences. A related aspect of the disclosure relates to pairs of such primers that can be used to amplify desired amplicons that contain a target nucleic acid sequence. These primers include one or more of the following primers pairs: a first Flu A primer pair, a second Flu A primer pair that can be used to amplify a region of the Flu A target nucleic acid that is different from the region of the Flu A target nucleic acid that can be amplified using the first Flu A primer pair, a Flu B primer pair, an RSV A primer pair, and an RSV B primer pair. These primer pairs include first and second primers that can be used generate corresponding amplicons for Flu A, Flu B, RSV A, and/or RSV B if the viral pathogen is present in the biological sample being tested.

In general, a primer pair includes a first primer that includes a priming nucleotide sequence that is substantially complementary to a first target nucleic acid sequence of viral genome a portion of which is to be amplified. Preferably, the first and second target nucleic acid sequences are spaced apart in the target nucleic acid by at least 10, and preferably by about 50-1,000 nucleotides, and each of them preferably consists of about 17 to about 100 contiguous bases of the viral genome to be detected. In some embodiments, one or more of the primers in one or more primer pairs further comprises a primer upstream region having a nucleotide sequence that is not complementary to the primer's target nucleotide sequence.

Preferred first primers for generating a first Flu A amplicon have the priming nucleotide sequence of SEQ NAME: FA1-A or SEQ NAME: FA1-W. Preferred second primers useful with such first primers have the priming nucleotide sequence of SEQ NAME: FA1-Y or SEQ NAME: FA1-AB. SEQ ID NOS: 1, 23, 25, & 28.

Preferred first primers for generating a second Flu A amplicon have the priming nucleotide sequence of SEQ NAME: FA2-B, SEQ NAME: FA2-C, SEQ NAME: FA2-D, SEQ NAME: FA2-E, or SEQ NAME: FA2-X. Preferred second primers useful with such first primers have the priming nucleotide sequence of SEQ NAME: FA2-Z or SEQ NAME: FA2-AA. SEQ ID NOS:2, 5, 24, 26, & 27.

Preferred first primers for generating a Flu B amplicon have the priming nucleotide sequence of SEQ NAME: FB-A or SEQ NAME: FB-Y. Preferred second primers useful with such first primers have the priming nucleotide sequence of SEQ NAME: FB-Z, SEQ NAME: FB-AA, and SEQ NAME: FB-AB. SEQ ID NOS:29 & 67 to 70.

Preferred first primers for generating an RSV A amplicon have the priming nucleotide sequence of SEQ NAME: RA-I or SEQ NAME: RA-N. Preferred second primers useful with such first primers have the priming nucleotide sequence of SEQ NAME: RA-B, SEQ NAME: RA-C, SEQ NAME: RA-D, SEQ NAME: RA-R, SEQ NAME: RA-S, SEQ NAME: RA-T, SEQ NAME: RA-U, and SEQ NAME: RA-V. SEQ ID NOS:79, 88, 72 to 74, & 92 to 96.

Preferred first primers for generating an RSV B amplicon have the priming nucleotide sequence of SEQ NAME: RB-A, SEQ NAME: RB-B, SEQ NAME: RB-C, and SEQ NAME: RB-U. Preferred second primers useful with such first primers have the priming nucleotide sequence of SEQ NAME: RB-F, SEQ NAME: RB-G, SEQ NAME: RB-U, and SEQ NAME: RB-Z. SEQ ID NOS:99 to 101, 104 to 106, & 115.

In some preferred embodiments, a probe and/or a primer contains one or more methylated cytosine bases.

Another related aspect of the disclosure concerns compositions that contain such probes, primers, and primer pairs. Such compositions include dry or liquid compositions. Dried compositions include lyophilized reagents containing one or more of a primer and a probe.

Another aspect of the disclosure relates to kits that include primers and/or probes. Such kits can also include salts, enzymes, dNTPs, dRTPs, other substrates, and/or instructions for use of such materials. The primers, probes, salts, enzymes, dNTPs, rNTPs, and/or other substrates of the kit may be in a dried form or in an aqueous form.

Another aspect of the disclosure relates to a reagent that contains primers and/or probes. Such reagents can also include salts, enzymes, dNTPs, rNTPs, and/or other substrates. The primers, probes, salts, enzymes, dNTPs, rNTPs, and/or other substrates of the reagents may be in a dried form or in an aqueous form.

Still another aspect of the disclosure concerns methods of using such primers and probes to analyze samples to determine if the sample contains one or more of a Flu A target nucleic acid, Flu B target nucleic acid, RSV A target nucleic acid, and RSV B target nucleic acid. The foregoing and other objects, features, and advantages of the compositions and methods will be apparent from the following detailed description and the claims.

DETAILED DESCRIPTION

Described herein are compositions, including kits and reagents, and methods for selectively detecting nucleic acids of various viral pathogens, specifically, Influenza A (Flu A), Influenza B (Flu B), Respiratory Syncytial Virus A (RSV A), and Respiratory Syncytial Virus B (RSV B), in a sample. These compositions and methods can be used, for example, in diagnostic applications, for screening clinical samples, nasopharyngeal samples, bronchoalveolar samples, donated blood and blood products or other tissues that may contain one or more of these pathogenic organisms.

As will be appreciated, any primer and probe sequences specific for Flu A, Flu B, RSV A, RSV B and/or other pathogenic viral target may be used as primers or probes in any suitable primer/probe-based in vitro nucleic acid amplification method adapted for amplification of an intended target nucleic acid. It is also understood that oligonucleotides having the sequences described herein could serve alternative functions in assays for detecting viral target nucleic acids. For example, a probe could be used as a primer (e.g., as one member of primer pair), and a primer could be used as a probe in an alternative detection assay.

The amplification primers are useful as components of uniplex or multiplex amplification reactions wherein amplicon species can be produced from target-specific primers in the reaction mixture. A multiplex amplification reaction includes primer pairs for amplifying two or more of Flu A, Flu B, RSV A, and RSV B, or, additionally includes primers for one or more of Flu A, Flu B, RSV A, and RSV B and one or more additional targets (e.g., human metapneumovirus, rhinovirus, adenovirus, parainfluenza virus, and/or *Bordetella*).

Amplification methods useful in connection with the present disclosure include: Polymerase Chain Reaction (PCR); Transcription-Mediated Amplification (TMA); Nucleic Acid Sequence-Based Amplification (NASBA); Strand Displacement Amplification (SDA); and amplification methods using self-replicating polynucleotide molecules and replication enzymes such as MDV-1 RNA and Q-beta enzyme. Methods for carrying out these various amplification techniques respectively can be found in U.S. Pat. Nos. 4,965,188; 5,399,491; 5,455,166; and 5,472,840, published European patent application EP 0 525 882, and Lizardi, et al., BioTechnology 6:1197 (1988). In particularly preferred embodiments, Flu A, Flu B, RSV A, and RSV B nucleic acid sequences are amplified using real-time PCR (RT-PCR).

Due to the lack of sequence conservation among respiratory virus strains, particularly for Flu A, and to accommodate for mismatches/mutations between a primer or a probe and their corresponding target nucleic acid sequences in viral target nucleic acid, degenerate bases and non-Watson Crick (NWC) base pairing can, in some preferred embodiments, be included in a primer or probe oligonucleotide. A NWC position in an oligonucleotide refers to a position where the oligonucleotide is configured to hybridize to at least one target nucleic acid sequence with a non-Watson Crick pairing, such as G-U, G-T, or G-A (either the G or the U/T/A can be the base in the oligonucleotide). In some embodiments, the NWC position is configured to hybridize via a wobble (G-U or G-T) or purine-purine (G-A) pair. In some embodiments, when one or more degenerate bases have been identified in the target nucleic acid sequence for a single primer or probe, multiple primer species or probe species may be synthesized in order to include all base combinations.

Useful guidelines for designing amplification primers and probes with desired characteristics are known in the art, and are described herein. The optimal sites for amplifying and probing Flu A, Flu B, RSV A, and RSV B nucleic acids contain two, and preferably three, conserved regions each greater than about 15 bases in length, all spatially separated from one another within a region of about 1,000, preferably of about 500, and even more preferably, of about 200 bases of contiguous sequence of the target nucleic acid. The degree of amplification observed with a set of primers depends on several factors, including the ability of the primers to hybridize to their complementary sequences and their ability to be extended enzymatically. Because the extent and specificity of hybridization reactions are affected by a number of factors, manipulation of those factors will determine the exact sensitivity and specificity of a particular oligonucleotide, whether perfectly complementary to its target or not. The effects of varying assay conditions are known in the art, see, e.g., U.S. Pat. No. 5,840,488.

Amplification primers and probes should be positioned to minimize the stability of oligonucleotide:nontarget (e.g., nucleic acid with similar sequence to target nucleic acid) and oligonucleotide:oligonucleotide (e.g., primer dimers and self-complementarity) nucleic acid hybrids. It is preferred that the amplification primers and detection probes be able to distinguish between target and non-target sequences. In designing primers and probes, the differences in their melting temperature (Tm) values for oligonucleotide:target compared to oligonucleotide:non-target and oligonucleotide:oligonucleotide should be as large enough to favor oligonucleotide:target hybridization. Also, long homopolymer tracts and high GC content are preferably avoided to reduce spurious primer extension.

As is known, nucleic acid hybridization involves the association of two single strands of complementary nucleic acid to form a hydrogen-bonded double strand. It is implicit that if one of the two strands is wholly or partially involved in a hybrid, then that strand will be less able to participate in formation of a new hybrid. By designing primers and probes so that substantial portions of the sequences of interest are single-stranded, the rate and extent of hybridization may be greatly increased. If the target is in a double-stranded form (as is the case with PCR products), denaturation prior to hybridization will typically be required.

Primers useful for conducting amplification reactions can have different lengths to accommodate the presence of extraneous sequences that do not participate in target binding, and that may not substantially affect amplification or detection procedures. For example, promoter-primers useful for performing amplification reactions in accordance with the disclosure have at least a minimal sequence that hybridizes to the desired target nucleic acid sequence, and a promoter sequence positioned upstream of that minimal sequence. However, insertion of sequences between the target binding sequence and the promoter sequence could change the length of the primer without compromising its utility in the amplification reaction. Additionally, the lengths of the amplification primers and detection probes are matters of choice as long as the sequences of these oligonucleotides conform to the minimal essential requirements for hybridizing with the desired complementary target sequence.

Hybridization assay probes useful for detecting Flu A, Flu B, RSV A, and RSV B nucleic acid sequences include a sequence of bases substantially complementary to the selected target nucleic acid sequence in the Flu A, Flu B, RSV A, or RSV B genome (or amplicon representing the corresponding region and its flanking or surrounding regions). Such probes may optionally have additional bases outside of the targeted nucleic acid region, which may or may not be complementary to Flu A, Flu B, RSV A, or RSV B nucleic acid.

Preferred probes are sufficiently homologous to the target nucleic acid to hybridize under stringent hybridization conditions corresponding to a designed amplification and detection reaction. For example, in PCR they extension and detection reactions are carried out such that an oligonucleotide would hybridize to its target nucleic acid sequence at a reaction temperature of about 60° C. Salt concentrations also impact hybridization of an oligonucleotide to its target nucleic acid sequence. An exemplary salt concentration is in a suitable range of about 0.6-0.9 M. Preferred salts include lithium chloride, but other salts such as sodium chloride and sodium citrate also can be used in the hybridization solution. Example high stringency hybridization conditions are also provided by 0.48 M sodium phosphate buffer, 0.1% sodium dodecyl sulfate, and 1 mM each of EDTA and EGTA, or by 0.6 M LiCl, 1% lithium lauryl sulfate, 60 mM lithium succinate and 10 mM each of EDTA and EGTA. Those skilled in the art are familiar with preparing solutions for nucleic acid hybridizations.

Probes in accordance with the disclosure have sequences complementary to, or corresponding to, a pre-selected target region of particular viral target nucleic acid targeted by the probe. Preferred probes have a probe sequence, which includes the target-hybridizing sequence of bases together with any base sequences that are not complementary to the nucleic acid that is to be detected, in the length range of from 10-100 nucleotides.

Amplification of nucleic acids by polymerase chain reaction (PCR) is a fundamental technique in molecular biology, typically requiring sample preparation, amplification, and product analysis. Although these steps are usually performed sequentially, amplification and analysis can occur simultaneously. DNA dyes or fluorescent probes can be added to the PCR mixture before amplification and used to analyze PCR products during amplification. Sample analysis occurs concurrently with amplification in the same tube within the same instrument. Such a combined approach decreases sample handling, saves time, and greatly reduces the risk of product contamination for subsequent reactions, as there is no need to remove the samples from their closed containers for further analysis. The concept of combining amplification with product analysis has become known as "real time" PCR (RT-PCR). See, for example, U.S. Pat. Nos. 6,174,670 and 8,137,616. In real time PCR, the formation of PCR products is monitored in each cycle of the PCR. The amplification is usually measured in thermocyclers that have additional devices for signal generation and detection from labels attached to probe oligonucleotide species during the amplification reaction. A number of such devices are known in the art for performing multiplex diagnostic assays with three, four, or more distinguishably labeled hybridization probes within one reaction vessel.

As is known, different formats exist for probe-based, real time detection of amplified DNA in multiplex assays. Common examples include "Taqman" probe systems, Molecular beacons and torches, single labeled probes, and FRET hybridization probes.

In TaqMan probe formats, a single-stranded hybridization probe for a given target is labeled with a donor/acceptor pair of detectable labels. When the donor (e.g., a fluorophore moiety) is excited with light of a suitable wavelength, the absorbed energy is transferred to the acceptor, (e.g., a quencher moiety), according to the principle of FRET. During the annealing step of a PCR reaction cycle, the hybridization probe binds to the target DNA and is degraded by the 5'-3' exonuclease activity of the Taq polymerase during the subsequent elongation phase. As a result, the excited donor moiety and the acceptor moiety become spatially separated, thus allowing for unquenched signal from the donor (e.g., a fluorescent emission) that is detected by the device. See, e.g., U.S. Pat. No. 5,538,848.

Molecular beacon and torch formats typically also include hybridization probes labeled with a donor/acceptor pair, with each of the donor moiety and the acceptor moiety being located at opposite ends of the probe. As a result of the secondary structure of the probe, which often involves hybridization of complementary regions at the ends of the probe, both the donor moiety and the acceptor moiety (e.g., the fluorescent moiety and the quencher moiety) are in spatial vicinity in solution. After hybridization of the probe's target hybridizing region to the desired target nucleic acid sequence, the donor moiety and the acceptor moiety are separated from one another such that after excitation of the donor moiety with light of a suitable wavelength its emission can be measured. See, e.g., U.S. Pat. No. 5,118,801.

In single label probe (SLP) formats, a single oligonucleotide is labeled with a single fluorescent dye at either the 5'- or 3'-end. Different designs can be used for oligonucleotide labeling, such as G-Quenching probes and Nitroindole-Dequenching probes. In G-Quenching embodiments, the fluorescent dye is attached via a C at the oligonucleotide's 5'- or 3'-end. Fluorescence decreases significantly when the probe is hybridized to the target if two G's are located on the target strand opposite to C and in position 1 aside of the complementary oligonucleotide probe. In the Nitroindole Dequenching embodiments, the fluorescent dye is attached to nitroindole at the 5'- or 3'-end of the oligonucleotide, and the itroindole decreases the fluorescent signaling from free (e.g., unhybridized) probe molecules. Fluorescence increases when the probe hybridizes to the target DNA due to a dequenching effect.

Multiplex assays that use FRET hybridization probes to detect target nucleic acids are particularly useful in homogenous hybridization assays (see, e.g., Matthews and Kricka, Analytical Biochemistry, vol. 169 (1988), pp: 1-25). In particular, the FRET hybridization probe format can be used in RT-PCR to detect amplified target DNA species.

Besides PCR and real time PCR, FRET hybridization probes can also be used for melting curve analysis. In such an assay, the target nucleic acid is amplified first in a typical PCR reaction with suitable amplification primers. The hybridization probes may already be present during the amplification reaction or added subsequently. After completion of the PCR reaction, the temperature of the sample is steadily increased, and fluorescence is detected as long as the hybridization probe is bound to the target DNA. At the melting temperature, the hybridization probe molecules are released from their complementary target sequences, and the fluorescent signal decreases immediately to the background level. This decrease is monitored with an appropriate fluorescence versus temperature-time plot such that a first derivative value can be determined, at which the maximum of fluorescence decrease is observed.

In some preferred embodiments, RT-PCR methods for amplifying and detecting multiple target DNA sequences in a multiplex assay are used. Such methods involve providing a composition or reaction mixture containing nucleic acids from biological sample, probes, primers, and a suitable polymerase activity to catalyze amplification, subjecting the reaction mixture to a thermocyling protocol such that amplification of the multiple target sequences occurs, and monitoring hybridization of each of the probe molecule species (e.g., pairs of FRET hybridization probes) at least once after a plurality of amplification cycles. In embodiments where the viral target nucleic acid(s) to be detected is/are comprised of one or more RNA molecules, such methods typically involve first converting RNA to DNA (e.g., a "complementary" DNA or "cDNA") through the use of a reverse polymerase activity.

In such multiplex embodiments, the composition or reaction mixture typically comprises at least 2, preferably 3-5, and most preferably 4 pairs of detection probes, preferably each pair of probes comprising a FRET donor moiety and a FRET acceptor moiety. In addition, such a composition or reaction mixture also comprises a number of reagents, including one or more of the following: buffers designed for PCR, dNTPs, a template dependent DNA polymerase (preferably a thermostable DNA polymerase), a reverse transcriptase.

During or after the amplification process is complete, the reaction is monitored to detect stable hybridization between one or more of the distinguishably labeled probe species present in the reaction and its corresponding target nucleic acid sequence (carried in an amplicon generated using the corresponding primer pair for the particular viral (or other) pathogen to be detected. Based on whether the donor moieties from each of the different donor/acceptor pairs are detected, it can then be determining if the biological sample contains Flu A, Flu B, RSV A, and/or RSV B and/or such other pathogens as are targeted in the particular assay.

Certain preferred kits will comprise one or more of a probe, a primer, a capture oligonucleotide, internal control oligonucleotides other ancillary oligonucleotides a buffer, dNTPs, DNA polymerase, reverse transcriptase, and instructions for using components of the kit (or a link to a website providing such instructions).

The following examples are provided to illustrate certain disclosed embodiments and are not to be construed as limiting the scope of this disclosure in any way.

General Reagents and Methods. Unless otherwise indicated, amplifications were performed using an ABI 7500 FAST® instrument. Viral isolates used as amplification targets or controls were diluted in suitable media, e.g., Micro Test M4 media (Remel Inc. Cat. No. R12500), Micro Test M5 Viral Transport Medium (Remel, Inc. Cat. No. R12515), Micro Test M6 Viral Transport Medium (Remel, Inc. Cat. No. R12530), Micro Test M4RT Viral Transport Medium (Remel, Inc. Cat. No. R12505), or Copan Universal Transport Medium (Copan Diagnostics, Inc., Cat. No. 330C). Nucleic acid was extracted from viral isolates using a non-specific target capture procedure as described in US Patent App. Pub. 2013/0209992.

PCR reaction mixtures were typically assembled as follows: 19.05 uL Supermix (Promega GoTaq® Supermix); 0.35 uL MMLV Reverse Transcriptase (35 U); 0.6 uL GoTaq MDX Hotstart Taq (3 U); 5 uL of nucleic acids (primers, probe, and target in suitable diluent); =25 uL total reaction volume. Promega, Madison, WI; New England Biolabs, Ipswich, MA; Sigma-Aldrich, St. Louis MO; Thermo Fisher, Waltham, MA; and others.

Example 1

Multiplex RT-PCT Assay to Detect Flu A, Flu B, RSV A, and RSV B

This example describes a representative RT-PCR assay based on Taqman reagent chemistry to provide for the detection and differentiation of Influenza A Virus, Influenza B Virus, and Respiratory Syncytial Virus Types A and B in a biological sample.

Here, the process begins by collecting, for example, a nasopharyngeal swab specimen from a symptomatic human patient. Unless the sample is to be immediately assayed, the sample is preferably placed in sealable container (e.g., an RNase/DNase-free 1.5 mL polypropylene microcentrifuge tube) along with an appropriate volume of viral transport medium (VTM; e.g., Remel, Inc., Copan Diagnostics, Inc., or (Becton, Dickinson and Co.). Preferably, a Universal Internal Control (UIC) is also then added to the sample to monitor for inhibitors that may be present in the sample.

Next, nucleic acids in the sample are isolated, for example, by using a MagNA Pure LC System (Roche) and a MagNA Pure Total Nucleic Acid Isolation Kit (Roche; cat. no. 03038505001) or a NucliSENS easyMAG System (bioMdrieux) and an Automated Magnetic Extraction Reagents (bioMdrieux). Purified nucleic acids are then added to a reaction mix along with a thermostable DNA polymerase and a reverse transcriptase. The reaction mix contains oligonucleotide primer pairs and target-specific oligonucleotide probes for each of Flu A, Flu B, RSV A, and RSV B, as well as Taq DNA polymerase, buffer containing dNTPs (dATP, dCTP, dGTP, dTTP (or dUTP)), $MgCl_2$, and stabilizers, and bovine serum albumin. For reverse transcription of viral genomes, M-MLV Reverse Transcriptase can be used, and to protect RNA from degradation, an RNase inhibitor (e.g., RNase Inhibitor II) can also be included. Various control nucleic acids may also be included. Such controls may be, for example, non-infectious in vitro transcribed RNA of specific viral sequences and/or non-infectious plasmid DNA containing control sequences. If desired, two different sets of amplification primers and probes targeting different genomic regions of the viruses to be detected can be used for any given target genome, particularly when, as may be the case with Flu A, genetic variation between strains may be such that detection based on a single region may be insufficient to assure accurate analysis. The amplification primers of the various primer pairs are complementary to highly conserved regions of genetic sequences for these respiratory viruses. The probe species are each dual-labeled with a distinguishable reporter dye and a quencher.

Reverse transcription of RNA into cDNA and subsequent amplification of DNA may be performed, for example, on a Cepheid SmartCycler II instrument (Cepheid, Sunnyvale, CA). In this process, for each viral genome to be detected, the probe species for the target viral genome (or region thereof) anneals specifically to the target nucleotide sequence of the target nucleic acid molecule (e.g., a specific region of the Flu A genome), followed by primer extension and amplification. The Taqman reagent chemistry utilizes the 5'-3' exonuclease activity of the Taq polymerase to cleave the probe, thus separating the reporter dye from its quencher. This generates an increase in fluorescent signal upon excitation from a light source. With each cycle, additional reporter dye molecules are cleaved from their respective probes, further increasing the fluorescent signal. The amount of fluorescence at any given cycle is dependent on the number of amplification products (amplicons) present at that time. Fluorescence intensity is monitored during each PCR cycle by the real-time instrument.

Example 2

Amplification and Detection of Flu A, Flu B, RSV A & RSV B in Clinical Samples

Remnant nasopharyngeal (NP) swab and lower and lower respiratory tract (LRT) specimens from individuals exhibiting signs and/or symptoms of a respiratory tract infection were analyzed in a multiplex real-time PCR assay using primers and probes for the amplification and detection of Flu A, Flu B, RSV A and RSV B target nucleic acids. NP swab and LRT samples were tested with the Panther Fusion Flu A/B/RSV assay.

For this example, 2930 remnant NP swab specimen were used. The specimen were processed to release nucleic acids. Briefly, remnant NP swab specimen were received in Remel transport media (Thermo Fisher, Waltham, MA). An aliquot of the transport media (500 ul) from each specimen was separately combined with a lysis reagent (710 ul) in a Panther Fusion Lysis Tube (Hologic, Marlborough, MA). Following an incubation, 360 ul of lysed specimen was combined with 450 ul of a target nucleic acid isolation reagent containing a capture oligonucleotide and a solid support. The target nucleic acid isolation reaction was performed on a Panther Fusion device (Hologic, Marlborough, MA), and as generally described in U.S. Pat. Nos. 6,110,678 & 9,051,601. Target nucleic acids isolated from each clinical specimen were then eluted from the capture reaction into a 50 ul eluate to provide 2930 sample conditions, each corresponding to one of the NP swab specimen. A nucleic acid amplification and detection reaction was set-up as follows: 5 ul from each sample condition was added to a well of a multiwall plate. Also contained within the well was 20 ul of a rehydrated real-time PCR reaction mixture. The dried PCR reaction mixture was rehydrated using 24 ul of a magnesium salt containing buffer. Components of this real-time PCR reaction mixture are described above and further comprised primers and probes with nucleotide sequences illustrated as SEQ ID NOS:5, 7, 12, 18, 23, 25 to 27, 64, 67, 68, 75, 79, 92, 101, 102, & 115. Probes for detecting Flu A amplification products were labeled with FAM/BHQ1, probes for detecting Flu B amplification products were labeled with CalRed/BHQ2, and probes for detecting RSV A and RSV B amplification products were labeled with CalOrange/BHQ1 (labels available from LGC Biosearch Technologies, Petaluma, CA). Each sample condition was independently added to a PCR reaction microtube. Control wells included an internal control, a positive control and a negative control.

Each PCR reaction microtube was then placed on a Panther Fusion device (Hologic, Inc., Marlborough, MA) and analyzed for the presence or absence of one or more of the target nucleic acids in each well. Of the 2930 NP swab specimen, 61 provided inconsistent results, and thus were deemed invalid and excluded from the evaluation results; 189/2869 (6.6%) were positive for Flu A target nucleic acid; 55/2869 (1.9%) were positive for Flu B target nucleic acid; and 365/2869 (12.7%) were positive for RSV A and/or RSV B.

A similar assay was performed using the remnant lower respiratory tract (LRT) specimen, with the exception that 250 ul of the LRT specimen was combined with 250 ul of lysis reagent, and then 360 ul of this combined solution was used for the target nucleic acid reaction. For this example, 144 remnant LRT specimen were used. The specimen were treated (specimen lysis, nucleic acid isolation, amplification, and detection) as is generally described above in this example. Of the 144 LRT specimen, 4 provided inconsistent results or were not tested, and thus were deemed invalid and excluded from the evaluation results; 3/140 (2.1%) were positive for Flu A target nucleic acid; 0/140 (0.0%) were positive for Flu B target nucleic acid; and 1/140 (0.7%) were positive for RSV A and/or RSV B.

These results show that the assay is a sensitive and specific assay for the detection of target nucleic acids from NP swab specimen. These results also show that the assay is sensitive for the detection of Flu A target nucleic acids, but on these LRT specimen sensitivity could not be determined for Flu B and RSV A & B target nucleic acids. These results show that the assay has high specificity for Flu A, Flu B, RSV A and RSV B target nucleic acids.

Example 3

Exemplary Oligonucleotide Sequences

Table 1 illustrates a number of primer and probe sequences that are useful as compositions, in kits, as diagnostic reagents, and/or in methods for the amplification or detection of one or more of Flu A, Flu B, RSV-A, and RSV-B. The following Table 1 illustrates only the nucleotide sequences. It is understood that these sequences may further include detectable labels, sugar modifications (e.g., 2'-methoxy), base modifications (e.g., a methylated base), and other chemical components that are not represented in the illustrated contiguous arrangements of symbols.

TABLE 1

| SEQ ID NO: | SEQ Name: | Sequence* | Oligo-nucleo-tide Type |
|---|---|---|---|
| SEQ ID NO: 1 | FA1-A | GATCTTGAGGCTCTCATG | Primer |
| SEQ ID NO: 2 | FA2-B | ATAACRTTCCATGGRGCCAA | Primer |
| SEQ ID NO: 3 | FA2-C | ATAACRTTCCATGGGGCCAA | Primer |
| SEQ ID NO: 4 | FA2-D | ATAACGTTCCATGGRGCCA | Primer |
| SEQ ID NO: 5 | FA2-E | ATAACGTTCCATGGGGCCAA | Primer |
| SEQ ID NO: 6 | FA1-F | CCCTTAGTCAGAGGTGACAG | Probe |
| SEQ ID NO: 7 | FA1-G | TCAGGCCCCCTCAAAGCCGAGATCGCC | Probe |
| SEQ ID NO: 8 | FA1-H | TCAGGCCCCCTCAAAGCCGA<u>R</u>ATCGC | Probe |
| SEQ ID NO: 9 | FA1-I | TCAGGCCCCCTCAAAGCCGA<u>G</u>ATCGC | Probe |
| SEQ ID NO: 10 | FA1*-J | 3'-AGUCCGGGGGAGUUUCGGCT<u>U</u>UAGCG-5' | Probe |
| SEQ ID NO: 11 | FA1*-K | 3'-AGUCCGGGGGAGUUUCGGCT<u>C</u>UAGCG-5' | Probe |

TABLE 1-continued

| SEQ ID NO: | SEQ Name: | Sequence* | Oligo-nucleo-tide Type |
|---|---|---|---|
| SEQ ID NO: 12 | FA1-L | AGCCAUTCCATGAGAGCCTCAAGATCC | Probe |
| SEQ ID NO: 13 | FA1-M | AGCCAYTCCATRAGAGCCTCAAGATC | Probe |
| SEQ ID NO: 14 | FA1-N | AGCCAUTCCATGAGAGCCTCAAGATC | Probe |
| SEQ ID NO: 15 | FA1*-O | 3'-UCGGUGAGGUACUCUCGGAGUUCUAG-5' | Probe |
| SEQ ID NO: 16 | FA1*-P | 3'-UCGGUAAGGUACUCUCGGAGUUCUAG-5' | Probe |
| SEQ ID NO: 17 | FA1*-Q | 3'-UCGGUAAGGUAUUCUCGGAGUUCUAG-5' | Probe |
| SEQ ID NO: 18 | FA2-R | CTGGTGCACTTGCCAGTTGUATGC | Probe |
| SEQ ID NO: 19 | FA2-S | CTGGTGCACTTGCCAGTTCYATG | Probe |
| SEQ ID NO: 20 | FA2-T | CTGGTGCACTTGCCAGTTCUATG | Probe |
| SEQ ID NO: 21 | FA2*-U | 3'-GACCACGUGAACGGUCAAGAUAC-5' | Probe |
| SEQ ID NO: 22 | FA2*-V | 3'-GACCACGUGAACGGUCAAGGUAC-5' | Probe |
| SEQ ID NO: 23 | FA1-W | CTTCTAACCGAGGTCGAAACGT | Primer |
| SEQ ID NO: 24 | FA2-X | ATAACGTTCCATGGGGCCAA | Primer |
| SEQ ID NO: 25 | FA1-Y | CCCTTAGTCAGAGGTGACA | Primer |
| SEQ ID NO: 26 | FA2-Z | CCCATTCTGTTGTATATGAG | Primer |
| SEQ ID NO: 27 | FA2-AA | CCCATCCTGTTGTATATGAG | Primer |
| SEQ ID NO: 28 | FA1-AB | GGTGAGCGTGAACACAAA | Primer |
| SEQ ID NO: 29 | FB-A | AGTGGAGGATGAAGAAGATGGC | Primer |
| SEQ ID NO: 30 | FB-B! | GCCTGCTTTGCCTTCTCCATCTTCTGTGCAGGC | Torch |
| SEQ ID NO: 31 | FB-B | GCCTGCTTTGCCTTCTCCATCTTCTG | Probe |
| SEQ ID NO: 32 | FB-C! | GCCTGCTTTGCCTTCTCCATCTTCTGTAGCAGGC | Torch |
| SEQ ID NO: 33 | FB-C | GCCTGCTTTGCCTTCTCCATCTTCTGT | Probe |
| SEQ ID NO: 34 | FB-D! | GCGCTAGTTCTGCTTTGCCTTCTCCATCTTCCTAGCGC | Torch |
| SEQ ID NO: 35 | FB-D | GCGCTAGTTCTGCTTTGCCTTCTCCATCTTC | Probe |
| SEQ ID NO: 36 | FB-E! | GCGCTAGTTCTGCTTTGCCTTCTCCATCTTCCTAGCGC | Torch |
| SEQ ID NO: 37 | FB-E | GCGCTAGTTCTGCTTTGCCTTCTCCATCTTC | Probe |
| SEQ ID NO: 38 | FB-F! | GCGCTAGTTCTGCTTTGCCTTCTCCATCTTCCTAGCGC | Torch |
| SEQ ID NO: 39 | FB-F | GCGCTAGTTCTGCTTTGCCTTCTCCATCTTC | Probe |
| SEQ ID NO: 40 | FB-G! | GCTGCTAGTTCTGCTTTGCCTTCTCCATCGCAGC | Torch |
| SEQ ID NO: 41 | FB-G | GCTGCTAGTTCTGCTTTGCCTTCTCCATC | Probe |
| SEQ ID NO: 42 | FB-H! | GCCTGCTAGTTCTGCTTTGCCTTCTCCATCGCAGGC | Torch |
| SEQ ID NO: 43 | FB-H | GCCTGCTAGTTCTGCTTTGCCTTCTCCATC | Probe |
| SEQ ID NO: 44 | FB-I! | GCCTGCTAGTTCTGCTTTGCCTTCTCCATCGCAGGC | Torch |
| SEQ ID NO: 45 | FB-I | GCCTGCTAGTTCTGCTTTGCCTTCTCCATC | Probe |
| SEQ ID NO: 46 | FB-J! | GCCTGCTAGTTCTGCTTTGCCTTCTCCATCAGCAGGC | Torch |
| SEQ ID NO: 47 | FB-J | GCCTGCTAGTTCTGCTTTGCCTTCTCCATC | Probe |
| SEQ ID NO: 48 | FB-K! | GCCTGCTAGTTCTGCTTTGCCTTCTCCATCAGCAGGC | Torch |
| SEQ ID NO: 49 | FB-K | GCCTGCTAGTTCTGCTTTGCCTTCTCCATC | Probe |

TABLE 1-continued

| SEQ ID NO: | SEQ Name: | Sequence* | Oligo-nucleo-tide Type |
|---|---|---|---|
| SEQ ID NO: 50 | FB-L! | GCCTGCTAGTTCTGCTTTGCCTTCTCCATCAGCAGGC | Torch |
| SEQ ID NO: 51 | FB-L | GCCTGCTAGTTCTGCTTTGCCTTCTCCATC | Probe |
| SEQ ID NO: 52 | FB-M! | GCCTGCTAGTTCTGCTTTGCCTTCTCCATCTAGCAGGC | Torch |
| SEQ ID NO: 53 | FB-M | GCCTGCTAGTTCTGCTTTGCCTTCTCCATC | Probe |
| SEQ ID NO: 54 | FB-N! | GCGGAGAAGGCAAAGCAGAAUTAGCAGTCTCCGC | Torch |
| SEQ ID NO: 55 | FB-N | GCGGAGAAGGCAAAGCAGAAUTAGCAG | Probe |
| SEQ ID NO: 56 | FB-O! | GCGGAGAAGGCAAAGCAGAAUTAGCAGTCTCCGC | Torch |
| SEQ ID NO: 57 | FB-O | GCGGAGAAGGCAAAGCAGAAUTAGCAG | Probe |
| SEQ ID NO: 58 | FB-P | TCTTTCCCACCRAACCAACA | Primer |
| SEQ ID NO: 59 | FB-Q | CTAGTTCTGCTTTGCCTTCTCCATCTTCT | Probe |
| SEQ ID NO: 60 | FB-R | AAGACTCCCACCGCAGTTTCAGCT | Probe |
| SEQ ID NO: 61 | FB-S | AAGACTCCCACCGCAGTTTCAGCT | Probe |
| SEQ ID NO: 62 | FB-T | AAGACTCCCACCGCAGTTTCAGCT | Probe |
| SEQ ID NO: 63 | FB-U | CTARTTCTGCTTTGCCTTCTCCATCTTCT | Probe |
| SEQ ID NO: 64 | FB-V | CTAGTTCTGCTTTGCCTTCTCCATCTTCT | Probe |
| SEQ ID NO: 65 | FB*-W | 3'-GAUUUAAGACGAAACGGAAGAGGUAGAAGA-5' | Probe |
| SEQ ID NO: 66 | FB*-X | 3'-GAUCAAGACGAAACGGAAGAGGUAGAAGA-5' | Probe |
| SEQ ID NO: 67 | FB-Y | GAGACACAATTGCCTACCTGCTT | Primer |
| SEQ ID NO: 68 | FB-Z | GAGTCTAGGTCAAAUTCTTTCCCACC | Primer |
| SEQ ID NO: 69 | FB-AA | GGTGCTCTTGACCAAATTGGG | Primer |
| SEQ ID NO: 70 | FB-AB | CTTTCCCACCRAACCAACAGTG | Primer |
| SEQ ID NO: 71 | RA-A | TTAGTCATYACAGTGACTGACAACAAAGG | Probe |
| SEQ ID NO: 72 | RA-B | AGGTAAGCTCCWAGATCTACTAT | Primer |
| SEQ ID NO: 73 | RA-C | AGGTAAGCTCCWAGATCTACTAT | Primer |
| SEQ ID NO: 74 | RA-D | AGGTAAGCTCCTAGATCTACTAT | Primer |
| SEQ ID NO: 75 | RA-E | TTAGTCATUACAGTGACTGACAACAAAGGAGC | Probe |
| SEQ ID NO: 76 | RA-F | TAGACCATGTGAATTCCCTGC | Probe |
| SEQ ID NO: 77 | RA-G | TTAGTCATYACAGTGACTGACAACAAAGG | Probe |
| SEQ ID NO: 78 | RA-H | TTAGTCATUACAGTGACTGACAACAAAGG | Probe |
| SEQ ID NO: 79 | RA-I | ACAAATGCAAAATCATACCTTACTC | Primer |
| SEQ ID NO: 80 | RA-J! | CGTGGCTTTATGTATTTGAATGCTCCTTTGGCCACG | Torch |
| SEQ ID NO: 81 | RA-J | CGTGGCTTTATGTATTTGAATGCTCCTTTG | Probe |
| SEQ ID NO: 82 | RA-K! | CGTGGCTTTATGTATTTGAATGCTCCTTTGGCCACG | Torch |
| SEQ ID NO: 83 | RA-K | CGTGGCTTTATGTATTTGAATGCTCCTTTG | Probe |
| SEQ ID NO: 84 | RA-L! | CGGTGGCTTTATGTATTTGAATGCTCCTTTGGCCACCG | Torch |
| SEQ ID NO: 85 | RA-L | CGGTGGCTTTATGTATTTGAATGCTCCTTTG | Probe |
| SEQ ID NO: 86 | RA-M! | CGGTGGCTTTATGTATTTGAATGCTCCTTTGAGCCACCG | Torch |

TABLE 1-continued

| SEQ ID NO: | SEQ Name: | Sequence* | Oligo- nucleo- tide Type |
|---|---|---|---|
| SEQ ID NO: 87 | RA-M | CGGTGGCTTTATGTATTTGAATGCTCCTTTG | Probe |
| SEQ ID NO: 88 | RA-N | ACAAATGCAAAAATCATACCTTACTC | Primer |
| SEQ ID NO: 89 | RA-O | TTAGTCATTACAGTGACTGACAACAAAGG | Probe |
| SEQ ID NO: 90 | RA-P | TTAGTCATYACAGTGACTGACAACAAAGG | Probe |
| SEQ ID NO: 91 | RA-Q | TTAGTCATUACAGTGACTGACAACAAAGG | Probe |
| SEQ ID NO: 92 | RA-R | AGGTAAGCTCCGAGATCTACTAT | Primer |
| SEQ ID NO: 93 | RA-S | CTAGGTAAGCTCCAAGATCTACTAT | Primer |
| SEQ ID NO: 94 | RA-T | CTAGGTAAGCTCCAAGATCTACTAT | Primer |
| SEQ ID NO: 95 | RA-U | CTAGGTAAGCTCCTAGATCTACTAT | Primer |
| SEQ ID NO: 96 | RA-V | CTAGGTAAGCTCCTAGATCTACTAT | Primer |
| SEQ ID NO: 97 | RA*-W | 3'-AAUCAGUAGUGUCACUGACUGUUGUUUCC-5' | Probe |
| SEQ ID NO: 98 | RA*-X | 3'-AAUCAGUAAUGUCACUGACUGUUGUUUCC-5' | Probe |
| SEQ ID NO: 99 | RB-A | TGAAGTTGATGAACAAAGTGG | Primer |
| SEQ ID NO: 100 | RB-B | GATGATGATCCYGCATCACTAAC | Primer |
| SEQ ID NO: 101 | RB-C | GATGATGATCCUGCATCACTAAC | Primer |
| SEQ ID NO: 102 | RB-D | ATGGGTGCCTATGTTCCAGTCATCTG | Probe |
| SEQ ID NO: 103 | RB-E | CACCAGCCCTCAATACCACCC | Probe |
| SEQ ID NO: 104 | RB-F | GCTTCAATGGTCCACAGTT | Primer |
| SEQ ID NO: 105 | RB-G | GCTTCAATGGTCCACAGTT | Primer |
| SEQ ID NO: 106 | RB-U | GATGATGATCCUGCATCACTAAC | Primer |
| SEQ ID NO: 107 | RB-V! | CGCTGCTGGCACAGATGACTGGAACATAGCAGCG | Torch |
| SEQ ID NO: 108 | RB-V | CGCTGCTGGCACAGATGACTGGAACATA | Probe |
| SEQ ID NO: 109 | RB-W! | CCGAGCAAGTCTGCTGGCACAGATGACTGGGCTCGG | Torch |
| SEQ ID NO: 110 | RB-W | CCGAGCAAGTCTGCTGGCACAGATGACTGG | Probe |
| SEQ ID NO: 111 | RB-X! | CCGAGCAAGTCTGCTGGCACAGATGACTGGTTGCTCGG | Torch |
| SEQ ID NO: 112 | RB-X | CCGAGCAAGTCTGCTGGCACAGATGACTGG | Probe |
| SEQ ID NO: 113 | RB-Y! | CGCCAGTCATCTGTGCCAGCAGACTTGCTGGCG | Torch |
| SEQ ID NO: 114 | RB-Y | CGCCAGTCATCTGTGCCAGCAGACTTG | Probe |
| SEQ ID NO: 115 | RB-Z | TAGTATGTTGATGCTTGCAAGTTC | Primer |

TABLE 1-continued

| SEQ ID NO: | SEQ Name: | Sequence* | Oligo-nucleo-tide Type |
|---|---|---|---|
| SEQ ID NO: 116 | Flu A | GenBank Accession No. KC355801.1 (13-JAN-13) | Target |
| SEQ ID NO: 117 | Flu B | GenBank Accession No. JX266956.1 (22-OCT-12) | Target |
| SEQ ID NO: 118 | RSV-A | GenBank Accession No. AY911262.1 (5-JUL-5) | Target |
| SEQ ID NO: 119 | RSV-B | GenBank Accession No. AF013254.1 (2-NOV-97 with non-se-quence changes on 30-SEP-99) | Target |

*All sequences are written in the 5' to 3' orientation unless indicated otherwise.
Sequence symbols are per Table 1 of World Intellectual Property Organization (WIPO) Handbook on Industrial Property Information and Documentation, Standard ST.25 (1998) ("WIPO ST.25 (1998)").
Sequence Names containing "!" are molecular torch probes.
Bold/underline on a symbol indicates degenerate or non-Watson/Crick residue relative to target.

All of the articles, devices, systems, and methods disclosed and claimed herein can be made and executed without undue experimentation in light of the present disclosure. While the devices, systems, and methods of this disclosure have been described in terms of preferred embodiments, it will be apparent to those of skill in the art that variations may be applied to the articles and methods without departing from the spirit and scope of the disclosure. All such variations and equivalents apparent to those skilled in the art, whether now existing or later developed, are deemed to be within the spirit and scope of the disclosure. It will also be appreciated that computer-based embodiments of the instant disclosure can be implemented using any suitable hardware and software.

All patents, patent applications, and publications mentioned in the specification are indicative of the levels of those of ordinary skill in the art to which the disclosure pertains. All patents, patent applications, and publications are herein incorporated by reference in their entirety for all purposes and to the same extent as if each individual publication was specifically and individually indicated to be incorporated by reference in its entirety for any and all purposes.

What is claimed is:

1. A kit for analysis of one or more Influenza A (Flu A) target nucleic acid molecule species that may be present in a biological sample, comprising:

(a) a first Flu A primer pair for generating a first Flu A amplicon if Flu A is present in the biological sample, the first Flu A primer pair comprising a first Flu A primer and a second Flu A primer, wherein:

(i) the first Flu A primer comprises a target hybridizing sequence consisting of the nucleic acid sequence of SEQ ID NO:23; and (ii) the second Flu A primer comprises a target hybridizing sequence consisting of the nucleic acid sequence of SEQ ID NO:25;

(b) a second Flu A primer pair for generating a second Flu A amplicon if Flu A is present in the biological sample, the second Flu A primer pair comprising a third Flu A primer and a fourth Flu A primer, wherein:

(i) the third Flu A primer comprises a target hybridizing sequence consisting of the nucleic acid sequence of SEQ ID NO:24; and (ii) the fourth Flu A primer comprises a target hybridizing sequence consisting of the nucleic acid sequence of SEQ ID NOs: 26 or 27;

(c) a first Flu A probe molecule species that is substantially complementary to a sequence in the first Flu A amplicon and comprises an oligonucleotide sequence comprising the nucleotide sequence of SEQ ID NO:7 or 12, wherein the first Flu A probe molecule species is linked to a fluorescent label; and (d) a second Flu A probe molecule species that is substantially complementary to a sequence in the second Flu A amplicon and comprises an oligonucleotide sequence comprising the nucleotide sequence of SEQ ID NO:18, wherein the first Flu A probe molecule species is linked to a fluorescent label.

2. The kit of claim 1, wherein one or more of the Flu A primers comprises a primer upstream region having a nucleotide sequence that is not complementary to a sequence present in the Flu A target nucleotide sequence.

3. The kit according to claim 1, further comprising one or more of:

(a) a Flu B primer pair for generating a Flu B amplicon if Flu B is present in the biological sample, the Flu B primer pair comprising a first Flu B primer and a second Flu B primer, wherein:

(i) the first Flu B primer comprises a target hybridizing sequence consisting of the nucleic acid sequence of SEQ ID NO:29 or 67; and (ii) the second Flu B primer comprises a target hybridizing sequence consisting of the nucleic acid sequence of SEQ ID NO:68 or 70;

(b) an RSV A primer pair for generating an RSV A amplicon if RSV A is present in the biological sample, the RSV A primer pair comprising a first RSV A primer and a second RSV A primer, wherein:

(i) the first RSV A primer comprises a target hybridizing sequence consisting of a nucleic acid sequence of SEQ ID NO:79 or 88; and (ii) the second RSV A primer comprises a target hybridizing sequence consisting of a nucleic acid sequence selected from the group consisting of: SEQ ID NOs: 72-74 and 92-96; and (c) an RSV B primer pair for generating an RSV B amplicon if RSV B is present in the biological sample, the RSV B primer pair comprising a first RSV B primer and a second RSV B primer, wherein:

(i) the first RSV B primer comprises a target hybridizing sequence consisting of the nucleic acid sequence selected from the group consisting of: SEQ ID NOs: 99 to 101 and 106; and (ii) the second RSV B primer comprises a target hybridizing sequence consisting of nucleic acid sequence of selected from the group consisting of: SEQ ID NOs: 104-106 and 115.

4. The kit of claim 3, wherein the kit contains (a) the Flu B primer pair;

(b) the RSV A primer pair;

(c) the RSV B primer pair;

(d) the Flu B primer pair and the RSV A primer pair;

(e) the Flu B primer pair and the RSV B primer pair;

(g) the RSV A primer pair and the RSV B primer pair; or (h) the Flu B primer pair, the RSV A primer pair, and the RSV B primer pair.

5. The kit of claim 4, wherein:

(c) if the kit contains the Flu B primer pair, then the kit further comprises a Flu B probe molecule species that is substantially complementary to a sequence in the Flu B amplicon, is about 17 to about 100 contiguous bases in length, and comprises an oligonucleotide sequence of any one of SEQ ID NOs: 30-66;

(d) if the kit contains the RSV A primer pair, then the kit further comprises a RSV A probe molecule species that is substantially complementary to a sequence in the RSV A amplicon, is about 17 to about 100 contiguous bases in length, and comprises an oligonucleotide sequence of any one of SEQ ID NOs: 71, 75-78, 80-87, 89-91, and 97-98; and (e) if the kit contains the RSV B primer pair, then the kit further comprises a RSV B probe molecule species that is substantially complementary to a sequence in the RSV B amplicon, is about 17 to about 100 contiguous bases in length, and comprises an oligonucleotide sequence of any one of SEQ ID NOs: 102, 103 and 107-114.

6. The kit of claim 4, wherein one or more of the primers comprises a primer upstream region having a nucleotide sequence that is not complementary to the primer's target nucleotide sequence.

7. The kit of claim 1, wherein the kit further comprises reagents to perform at least one nucleic acid amplification reaction.

8. The kit of claim 7, wherein the kit further comprises instructions for using the primer pair species and the reagents to perform the at least one nucleic acid amplification.

9. The kit of claim 1, wherein at least one primer or at least one probe molecule species is present in the kit as a lyophilized reagent.

10. The kit of claim 7, wherein the kit comprises one or more of: a reverse transcriptase, a DNA polymerase, a buffer, and dNTPs.

11. The kit of claim 10, wherein the kit comprises a reverse transcriptase, a DNA polymerase, a buffer, and dNTPs.

12. The kit of claim 11, wherein the reverse transcriptase, the DNA polymerase, the buffer, and the dNTPs are present in the kit as a lyophilized reagent.

13. The kit of claim 12, further comprising a rehydration reagent comprising a salt.

14. The kit of claim 13, wherein the salt is a magnesium salt.

15. The kit of claim 1, wherein the first Flu A primer comprises a nucleic acid sequence consisting of the nucleic acid sequence of SEQ ID NO:23, the second Flu A primer comprises a nucleic acid sequence consisting of the nucleic acid sequence of SEQ ID NO: 25, the third Flu A primer comprises a nucleic acid sequence consisting of the nucleic acid sequence of SEQ ID NO:24, and the fourth Flu A primer comprises a nucleic acid sequence consisting of the nucleic acid sequence of SEQ ID NO:26 or 27.

16. The kit of claim 5, wherein each probe molecule species is labeled with one or more detectable labels selected from the group consisting of: a chemiluminescent moiety, a fluorophore moiety, a quencher moiety, and both a fluorophore moiety and a quencher moiety.

17. The kit of claim 16, wherein at least one of the probe molecule species is distinguishably labeled such that the at least one probe molecule species can be distinguished from the other probe molecule species.

18. The kit of claim 1, wherein the one or more of the probe molecule species is detectably labeled with a donor/acceptor label pair.

19. The kit of claim 1, wherein at least one primer and/or at least one probe molecule species contains one or more methylated cytosine bases.

20. A method for determining the presence or absence of a Flu A target nucleic acid, and one or more of a Flu B target nucleic acid, an RSV A target nucleic acid, and an RSV B target nucleic acid in a biological sample, the method comprising the steps of:

(a) providing the kit of claim 5 and contacting the biological sample with the first Flu A primer pair, second Flu A primer pair, the first Flu A probe molecule species, the second Flu A probe molecule species, the one of more of the Flu B primer pair, the RSV A primer pair, and the RSV B primer pair, and the Flu B probe molecule species, the RSV A probe molecule species, and/or the RSV B probe molecule species of claim 5;

(b) performing an in vitro nucleic acid amplification reaction wherein:

(i) the Flu A target nucleic acid, if present in the biological sample, is used by the first Flu A primer pair to generate the first Flu A amplicon and/or the second Flu A primer pair to generate the second Flu A amplicon;

(ii) the Flu B target nucleic acid, if present in the biological sample, is used by the Flu B primer pair to generate the Flu B amplicon;

(iii) the RSV A target nucleic acid, if present in the biological sample, is used by the RSV A primer pair to generate the RSV A amplicon; and (iv) the RSV B target nucleic acid, if present in the biological sample, is used by the RSV B primer pair to generate the RSV B amplicon; and (c) detecting the presence of absence of the first Flu A amplicon, the second Flu A amplicon, the Flu B amplicon, the RSV A amplicon, and/or the RSV B amplicon, wherein detecting the presence of an amplicon indicates the presence of the corresponding target nucleic acid in the biological sample.

21. The method of claim 20, wherein the detecting is performed in real time.

22. A reaction mixture comprising a first Flu A primer pair, a second Flu A primer pair, a first Flu A probe molecule species and a second Flu A probe molecule species wherein:

(a) the first Flu A primer pair generates a first Flu A amplicon if Flu A is present in a biological sample, the first Flu A primer pair comprises:

(i) a first Flu A primer comprising a target hybridizing sequence consisting of the nucleic acid sequence of SEQ ID NO:23; and (ii) a second Flu A primer comprising a target hybridizing sequence consisting of the nucleic acid sequence of SEQ ID NO:25;

(b) the second Flu A primer pair generates a second Flu A amplicon if Flu A is present in the biological sample, the second Flu A primer pair comprises:

(i) a third Flu A primer comprising a target hybridizing sequence consisting of the nucleic acid sequence of SEQ ID NO:24; and (ii) a fourth Flu A primer comprising a target hybridizing sequence consisting of the nucleic acid sequence of SEQ ID NOs: 26 or 27;

(c) a first Flu A probe molecule species that is substantially complementary to a sequence in the first Flu A amplicon and comprises an oligonucleotide sequence comprising the nucleotide sequence of SEQ ID NO:7 or 12, wherein the first Flu A probe molecule species is linked to a fluorescent label; and (d) a second Flu A probe molecule species that is substantially complementary to a sequence in the second Flu A amplicon and comprises an oligonucleotide sequence comprising the nucleotide sequence of SEQ ID NO:18, wherein the first Flu A probe molecule species is linked to a fluorescent label.

23. The kit of claim 6, wherein the first Flu A probe molecule species comprises a first probe comprising an oligonucleotide sequence comprising the nucleotide sequence of SEQ ID NO:7 and a second probe comprising an oligonucleotide sequence comprising the nucleotide sequence of SEQ ID NO: 12.

24. The reaction mixture of claim 22, wherein the first Flu A probe molecule species comprises a first probe comprising an oligonucleotide sequence comprising the nucleotide sequence of SEQ ID NO:7 and a second probe comprising an oligonucleotide sequence comprising the nucleotide sequence of SEQ ID NO: 12.

* * * * *